(12) United States Patent
Tobola et al.

(10) Patent No.: US 8,295,901 B2
(45) Date of Patent: Oct. 23, 2012

(54) SPECTRAL ANALYSIS FOR A MORE RELIABLE DETERMINATION OF PHYSIOLOGICAL PARAMETERS

(75) Inventors: Andreas Tobola, Erlangen (DE); Ulrich Vogl, Ebermannsdorf (DE); Hans-Joachim Moersdorf, Fuerth (DE)

(73) Assignee: Fraunhofer-Gesellschaft zur Foerderung der angewandten Forschung E.V., Munich (DE)

( * ) Notice: Subject to any disclaimer, the term of this patent is extended or adjusted under 35 U.S.C. 154(b) by 1347 days.

(21) Appl. No.: 11/676,190

(22) Filed: Feb. 16, 2007

(65) Prior Publication Data

US 2008/0027299 A1 Jan. 31, 2008

(30) Foreign Application Priority Data

Feb. 20, 2006 (DE) .......................... 10 2006 007 879
May 11, 2006 (DE) .......................... 10 2006 022 056

(51) Int. Cl.
*A61B 5/1455* (2006.01)
*A61B 5/02* (2006.01)
(52) U.S. Cl. ......... 600/323; 600/310; 600/324; 600/502
(58) Field of Classification Search .................. 600/310, 600/322, 323, 316, 324, 326, 331, 473, 476, 600/517; 708/446, 520
See application file for complete search history.

(56) References Cited

U.S. PATENT DOCUMENTS

| | | | | |
|---|---|---|---|---|
| 5,503,148 | A | | 4/1996 | Pologe |
| 5,560,367 | A | * | 10/1996 | Haardt et al. ................. 600/515 |
| 5,630,413 | A | * | 5/1997 | Thomas et al. ............... 600/310 |
| 5,921,921 | A | | 7/1999 | Potratz et al. |
| 6,002,952 | A | * | 12/1999 | Diab et al. .................... 600/310 |
| 6,334,065 | B1 | * | 12/2001 | Al-Ali et al. .................. 600/323 |
| 6,411,833 | B1 | * | 6/2002 | Baker et al. ................... 600/336 |
| 6,587,701 | B1 | * | 7/2003 | Stranc et al. .................. 600/310 |
| 6,714,803 | B1 | | 3/2004 | Mortz |
| 2002/0012008 | A1 | | 1/2002 | Takagi |
| 2002/0136264 | A1 | | 9/2002 | Herleikson et al. |
| 2004/0030229 | A1 | * | 2/2004 | Norris ........................... 600/323 |
| 2004/0204638 | A1 | | 10/2004 | Diab et al. |
| 2004/0225225 | A1 | | 11/2004 | Naumov et al. |
| 2005/0187451 | A1 | | 8/2005 | Norris |
| 2007/0255779 | A1 | | 11/2007 | Watts, III |

FOREIGN PATENT DOCUMENTS

| | | |
|---|---|---|
| DE | 69229994 | 10/1999 |
| EP | 208201 | 1/1987 |
| EP | 314331 | 5/1989 |
| EP | 341059 | 11/1989 |
| EP | 0502717 | 9/1992 |
| EP | 1254628 | 11/2002 |
| EP | 1357481 A2 | 10/2003 |
| EP | 1374764 | 1/2004 |
| WO | WO 98/17172 | 4/1998 |
| WO | WO02054950 | 7/2002 |

* cited by examiner

*Primary Examiner* — Eric Winakur
*Assistant Examiner* — Chu Chuan (JJ) Liu
(74) *Attorney, Agent, or Firm* — Michael A. Glenn; Glenn Patent Group

(57) ABSTRACT

An apparatus for determining a spectral ratio between a first signal having a first spectrum which depends on a biological quantity, and a second signal having a second spectrum which depends on a biological quantity, the first signal and the second signal having a plurality of harmonics of a periodic signal, the apparatus including a computer for computing a first wave ratio between a spectral value of the first spectrum which has a frequency of a harmonic of the plurality of harmonics, and a spectral value of the second spectrum which has the frequency of the harmonic; and for computing a second wave ratio between a spectral value of the first spectrum which has a frequency of another harmonic of the plurality of harmonics, and a spectral value of the second spectrum which has the frequency of the other harmonic. In addition, the apparatus includes an optimizer.

25 Claims, 23 Drawing Sheets

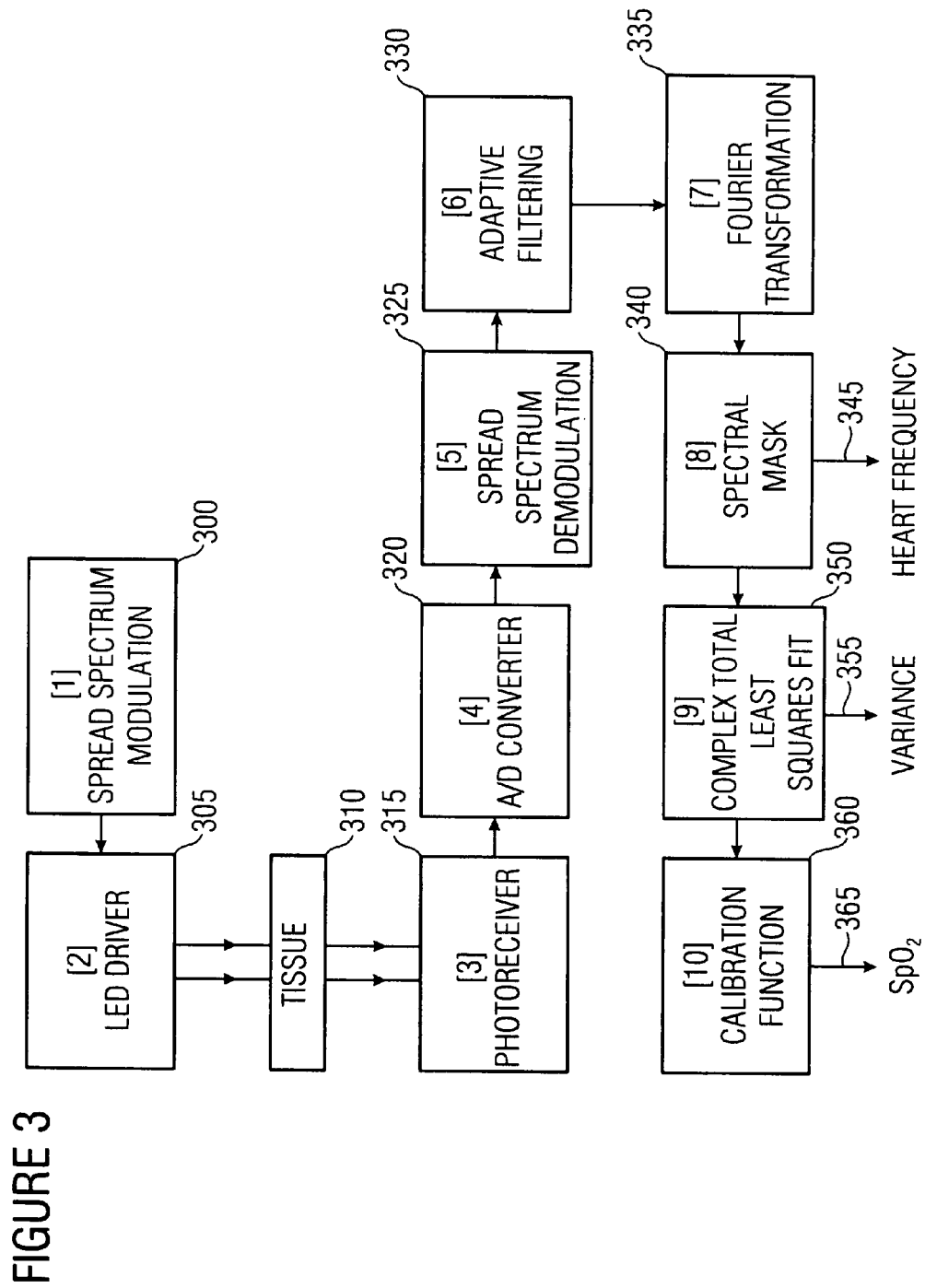

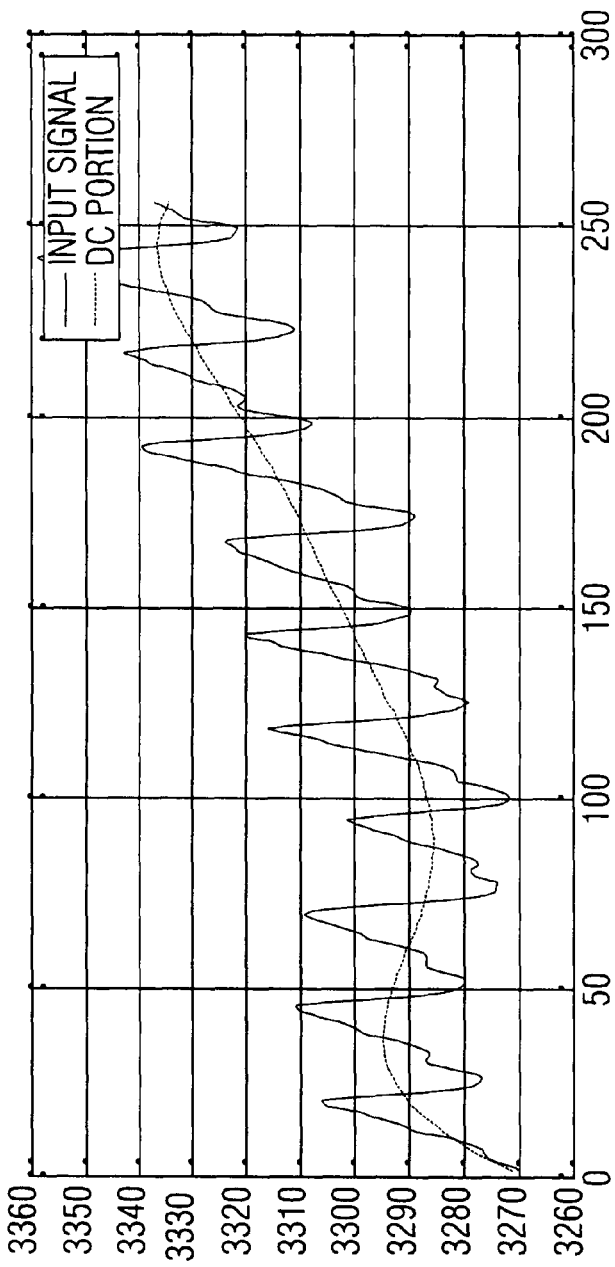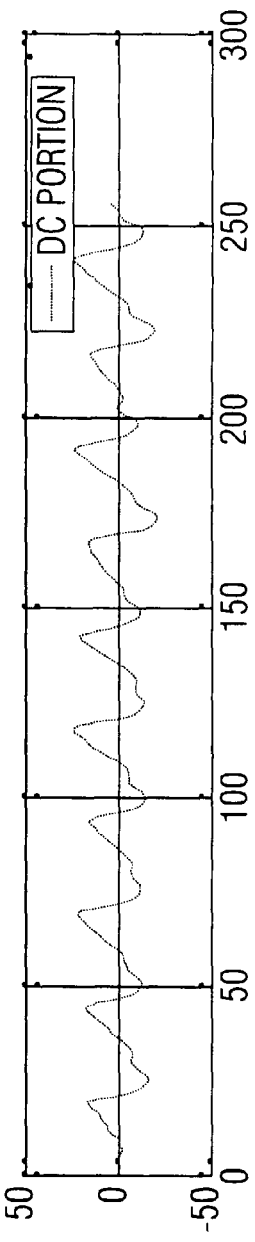
FIGURE 15A
FIGURE 15B

SPECTRAL ANALYSIS FOR A MORE RELIABLE DETERMINATION OF PHYSIOLOGICAL PARAMETERS

CROSS-REFERENCE TO RELATED APPLICATION

This application claims priority from German Patent Application No. 102006007879.9, which was filed on Feb. 20, 2006, and is incorporated herein by reference in its entirety.

TECHNICAL FIELD

The present invention relates to an apparatus for determining a spectral ratio of two spectra of two time-discrete signals for a more reliable determination of a physiological parameter from the spectral ratio and the spectra. The method may be applied in plethysmogram-based measuring methods (e.g. plethysmography, pulse oximetry) for the purpose of a reduced susceptibility to ambient-light interferences and electromagnetic interferences.

BACKGROUND

Plethysmography is an optical method of obtaining a so-called plethysmogram which provides information about the pulse frequency and the oxygen saturation of the blood of a test person. A plethysmogram is a graphic illustration of volume changes. In this field of application, it is specifically the volume changes of an arterial blood flow at a localized measurement site of the human body which are detected as the plethysmogram. To implement this in technical terms, light is radiated through tissue at a body location having arterial blood vessels. The patient has a sensor applied to him/her which contains a light source and a photoreceiver, so that the light passes through the tissue layer, and so that the remaining light intensity impinges upon the photoreceiver. Within the body, the light undergoes an attenuation which is dependent, among other things, on the wavelength of the light source, the type and concentration of the substances in the irradiated tissue, and on the pulsation of the blood. The signal of the photoreceiver which has thus been obtained is present in the form of a photocurrent, is dependent on the above-mentioned general conditions, and corresponds, in a first approximation, to the changes in the blood volume of arterial vessels which are caused by contraction of the heart muscle. FIG. 25 shows the basic architecture of an apparatus for detecting a plethysmogram. A microcontroller (µC) controls, via two driver stages, two LEDs of different wavelengths, one light source being sufficient, in principle, for creating a plethysmogram. The LEDs depicted in FIG. 25 emit light in the red and infrared regions. The light emitted by the LEDs subsequently passes through the tissue of the test person, in FIG. 25 this is depicted, by way of example, as a finger. Once the light has passed through the tissue of the test person, it will impinge upon a photosensor. The photsensor converts the optical signals into electrical signals and passes them on to processing electronics which amplify the signal, convert them from analog to digital and feed them to the microcontroller (µC). The microcontroller (µC) then determines two plethysmograms, one plethysmogram for each wavelength, from the digital signals fed to it. From the waveforms of the plethysmograms thus measured, physiological parameters, such as the heart frequency or the oxygen saturation of the test person's blood, may be measured, with one single plethysmogram being sufficient, in principle, for determining the heart frequency, for determining the oxygen saturation of the blood, two plethysmograms of light sources of different wavelengths being necessary.

Pulse oximetry is a non-invasive method of measuring the oxygen saturation of the blood ($SpO_2$) and the heart frequency (HR) by means of an optical sensor. The oxygen saturation detected by the pulse oximeter is specifically referred to as the $SpO_2$ value. The oxygen saturation is defined as the ratio of the concentration of oxygen-saturated hemoglobin molecules and the overall hemoglobin concentration, and is indicated in percent. A component of the pulse oximeter is a sensor having two integrated light sources and being configured similar to a plethysmograph, cf. FIG. 25. In pulse oximetry, use is made of at least two plethysmograms to determine the color of the arterial blood. The color of the blood, in turn, is dependent on the oxygen saturation. By selecting the wavelengths of the light sources well, it may be shown that a quantity correlating well with the oxygen saturation may be obtained from the ratios of prominent points within the plethysmogram. Typically, the spectra of the receive signals of two light sources of different wavelengths are determined, and the quotient of specific spectral values is formed. This quotient will then be approximately proportional to the $SpO_2$ value of the blood.

An essential quality characteristic in comparing pulse oximeters is the resistance toward interferences. Filtering those unuseful signal portions which arise because of the movement of the patient is particularly problematic. Even with small movements, the amplitudes of the motion artifacts may seem larger than those of the pulse wave within the signal. If the signal is highly overlaid by motion artifacts, this will lead to a temporary operational failure of the equipment, with this problem being signaled accordingly. In the worst case, the equipment will not detect the distorted measurement and will not issue a signal, so that the measurement values indicated will erroneously be held as true. The quality of treatment of a patient may be clearly reduced due to measurement values being incorrectly indicated. Especially in the environment of operating rooms, the above-mentioned distortions represent a major disadvantage of pulse oximeters.

In addition to the motion artifacts, high-power light sources, such as those of operating-room lamps, fluorescent lamps or monitors, may cause unwanted interferences in the signal. With conventional pulse oximeters or plethysmographs, this problem is typically diminished by introducing additional measurement periods for determining the ambient light, and by subsequently subtracting the ambient-light measurement from the useful-signal measurement. During these measurement periods or time slots, all light sources of the sensor are switched off, and only the ambient light is measured. The ambient-light intensity is subtracted from the plethysmogram, and thus the portion of ambient light is largely separated from the pulse signal. However, especially with pulsating or AC-powered ambient-light sources, an interference portion will remain within the plethysmogram. The interference portion within the plethysmogram thus highly depends on the electronic equipment, or interferers, used in the surroundings. Especially in the intensive care of patients, a multitude of electronic devices and tools are employed, so that the susceptibility of pulse oximeters and plethysmographs to interference is a given fact particularly in intensive-care environments. Particularly in the field of intensive care, however, measurement errors of physiological parameters such as the heart frequency or the blood oxygen saturation are extremely critical and may entail serious consequences.

In pulse oximetry, transmission and remission sensors have several LEDs (transmitters) and only one photodiode (receiver). The test person's tissue is irradiated by LEDs of different wavelengths, and the photodiode receives the light of different wavelengths from the tissue. In principle, it would be possible to differentiate various channels by means of the wavelengths of the LEDs, e.g. by color filters present at several photodiodes. Since this involves a large amount of technical expenditure on the side of the photodiode, the intensities of the LEDs must be modulated. Only then is it possible to differentiate between the wavelengths by means of a single broad-band photodiode.

In order to enable the receiver to differentiate between various transmit sources (LEDs) having different wavelengths, TDMA concepts (time division multiple access) are employed with known pulse oximeters. Each sensor LED has a time window assigned to it within which it is switched on. FIG. 26 illustrates this time sequence of signals. One may recognize that the various LEDs successively have time slots of equal durations associated with them which are separated by dark periods of equal durations. FIG. 26 shows a schematic sequence with three different LEDs. The LEDs of different wavelengths successively light up for a short time duration, in FIG. 26, the bright periods of the LEDs are designated by "LED 1", "LED 2", and "LED 3". Typical frequencies with which the light sources of current pulse oximeters are controlled amount to 20-50 Hz. By adding additional dark phases during which none of the LEDs lights up, designated by "DARK" in FIG. 26, one tries to measure the signal portion caused by ambient light, and to subsequently subtract it from the useful signal. Nevertheless, the results are often distorted by ambient light or by high-frequency surgery influences. In high-frequency surgery, tissue is cut by means of high-frequency voltages. These high frequencies cause inductions in lines of the pulse oximeters and may thus interfere with their functioning. The local influences may be largely suppressed, since the sensors are protected against irradiation from the outside. Nevertheless, ambient light will enter into the shell of the sensor.

A further example of dynamic interferences may be found with test persons who have long-term measurements conducted on them. They wear a sensor with integrated LEDs and a photoreceiver over a relatively long time period for detecting long-term data. These patients or test persons, for example during car journeys through tree-lined streets or streets lined by many high buildings, are subject to pronounced and, as the case may be, rapid changes in the lighting conditions. In places, these changing lighting conditions express themselves in a manner very similar to the interferences in in-patient environments of hospitals. In principle, test persons subjected to long-term measurements are exposed to a multiplicity of ambient-light influences which may give rise to a whole spectrum of interferences.

The signal quality is clearly improved by subtracting the ambient-light portion, determined by adding dark phases. However, interference artifacts will remain which may lead to incorrect $SpO_2$ values. Up to now, it has not been possible, despite numerous attempts, to remove those interferences, which are caused by fluorescent lamps, infrared heat lamps, operating-room illumination and monitors, from the useful signal. Since in pulse oximeters and plethysmographs, the ratio between useful signals, i.e. those signal portions caused by the change in volume of the tissue, and the interferences may be very unfavorable, those interferences which are distorted further by signal processing are also relevant. For example, prior to an analog/digital conversion, signals are low-pass filtered to avoid errors caused by subsampling. Since the filters used only ever have a finite attenuation within the stop band, errors caused by subsampling, also referred to as aliasing errors, will nevertheless arise. Depending on the original interfering frequency, these interferences will then be mirrored into the useful range, where they may occur at different frequencies.

The susceptibility of current pulse oximeters and plethysmographs to interferences will rise if the above-mentioned interferers are located within their surroundings. Especially in operating rooms or intensive-care units, there are a multiplicity of electronic devices, or electronic interferers. Particularly in such environments, thus, the susceptibility of current pulse oximeters and plethysmographs to interferences increases. This significant disadvantage may entail serious consequences for test persons if such situations give rise to measurement errors which cannot be immediately identified as such.

Known plethysmography methods may be found in the following documents, for example:

EP 1374764 A1/WO 2002054950 A08, which describes a basic circuit for measuring and detecting a plethysmogram, and deals with the above-described signal processing in detail.

EP 208201 A2/A3, wherein optical detection of a change of volume of a body part, and an evaluation device for evaluating the optical signals are protected, in principle. The method described there makes use of the changing outward volume change of extremities caused by the pulse and the changes in blood pressure associated therewith.

EP 341059 A3. Here, a basic pulse oximetry method is described which exploits light sources (LEDs) of different wavelengths. Light of different wavelengths is radiated through the test person's tissue, the light signals are absorbed from the tissue by means of optical sensors and are evaluated by a corresponding analog signal processing.

EP 314331 B1, a pulse oximetry method also based on light of different wavelengths is used for radiating through the tissue of a test person. The optical signals thus obtained are converted to electric signals, and a value which provides insights into the oxygen saturation of the test person's blood is extracted therefrom.

EP 1254628 A1, the pulse oximeter protected here is also configured to determine oxygen saturation of blood, the method proposed here additionally reducing interferences caused by cross-talk.

U.S. Pat. No. 5,503,144/U.S. Pat. No. 6,714,803, here a description is given of signal processing methods for linear regression which determine an $SpO_2$ value by means of two plethysmograms. A correlation coefficient which serves as the reliability measure is determined from among the two plethysmograms.

SUMMARY

According to an embodiment, an apparatus for determining a spectral ratio between a first signal having a first spectrum which depends on a biological quantity, and a second signal having a second spectrum which depends on a biological quantity, the first signal and the second signal having a plurality of harmonics of a periodic signal, may have: a computer for computing a first wave ratio between a spectral value of the first spectrum which has a frequency of a harmonic of the plurality of harmonics, and a spectral value of the second spectrum which has the frequency of the harmonic; and for computing a second wave ratio between a spectral value of the first spectrum which has a frequency of another harmonic of the plurality of harmonics, and a spectral value of the second spectrum which has the frequency of the other harmonic; an optimizer for determining the spectral ratio while using the first and second wave ratios, the optimizer being configured to determine the spectral ratio such that it differs from the first wave ratio and the second wave ratio, and meets an optimization criterion.

According to another embodiment, a method for determining a spectral ratio between a first signal having a first spectrum which depends on a biological quantity, and a second signal having a second spectrum which depends on a biological quantity, the first signal and the second signal having a plurality of harmonics of a periodic signal, may have the steps of: computing a first wave ratio between a spectral value of the first spectrum which has a frequency of a harmonic of the plurality of harmonics, and a spectral value of the second spectrum which has the frequency of the harmonic; computing a second wave ratio between a spectral value of the first spectrum which has a frequency of another harmonic of the plurality of harmonics, and a spectral value of the second spectrum which has the frequency of the other harmonic; determining the spectral ratio while using the first and second wave ratios, the spectral ratio being determined such that it differs from the first and second wave ratios and meets an optimization criterion.

The object is achieved by an apparatus for determining a spectral ratio between a first signal having a first spectrum which depends on a biological quantity, and a second signal having a second spectrum which depends on the biological quantity, the first signal and the second signal having a plurality of harmonics of a periodic signal. In addition, the apparatus comprises a computer for computing a first wave ratio between a spectral value of the first spectrum which has a frequency of a harmonic of the plurality of harmonics, and a spectral value of the second spectrum which has the frequency of the harmonic. In addition, the computer serves to compute a second wave ratio between a spectral value of the first spectrum which has a frequency of another harmonic of the plurality of harmonics, and a spectral value of the second spectrum which has the frequency of the other harmonic. Also, the apparatus comprises an optimizer for determining the spectral ratio and the use of the first and second wave ratios, the optimizer being configured to determine the spectral ratio such that it differs from the first and the second wave ratios and meets an optimization criterion.

In addition, the object is achieved by a method for determining a spectral ratio between a first signal having a first spectrum which depends on a biological quantity, and a second signal having a second spectrum which depends on a biological quantity, the first signal and the second signal having a plurality of harmonics of a periodic signal, by computing a first wave ratio between a spectral value of the first spectrum which has a frequency of a harmonic of the plurality of harmonics, and a spectral value of the second spectrum which has the frequency of the harmonic. In addition, the method comprises the step of computing a second wave ratio between a spectral value of the first spectrum which has a frequency of another harmonic of the plurality of harmonics, and a spectral value of the second spectrum which has the frequency of the other harmonic. Also, the method comprises the step of optimizing for determining the spectral ratio while using the first and second wave ratios, the spectral ratio being determined such that it differs from the first and second wave ratios and meets an optimization criterion.

The core idea of the present invention is to more effectively suppress those interference portions which are overlaid on the useful signal in plethysmography and pulse oximetry, by exploiting the knowledge of the spectral composition of the useful signals. For determining the oxygen content of the blood, in plethysmography, two spectra of signals are determined which are due to optical receive signals of radiated-through tissue and have different wavelengths. Since both spectra are overlaid by interfering signals which may possibly be intense, one exploits, in the present invention, the knowledge of the shape and spectral composition of the pulse signal, one initially determines these frequency portions and determines the oxygen content of the blood on the basis of the frequencies thus determined. Initially, a reference spectrum is determined from the two spectra which are based on the optical receive signals of different wavelengths, independent interferences already being reduced within said reference spectrum. Within this reference spectrum, a search is now conducted for the frequency portions of a pulse signal, and once these characteristic frequency portions have been found, a linear coefficient is formed, on the basis of same, which may then be determined with a considerably higher level of reliability. Both when determining the reference spectrum and when determining the liner coefficient, use may be made of a mathematical method, so-called singular-value decomposition, which enables the reference spectrum and the linear coefficient to be determined with a minimum amount of imprecision.

BRIEF DESCRIPTION OF THE DRAWINGS

Embodiments of the present invention will be detailed subsequently referring to the appended drawings, in which:

FIG. 3 is block diagram of an implementation of the embodiment;

FIG. 9a) is a schematic representation of the spectrum within the baseband;

FIG. 9b) is a schematic representation of the spectrum of the chip sequence;

FIG. 9c) is a schematic representation of the spectrum within the transmission band;

FIG. 9d) is a schematic representation of the spectrum of the useful portions and interference portions within the baseband after de-spreading;

FIG. 15a) shows an exemplary waveform of an input signal and of the low-pass filtered DC signal (DC portion);

FIG. 15b) shows an exemplary waveform of the high-pass filtered signal (AC portion);

DETAILED DESCRIPTION

Figure 1A:
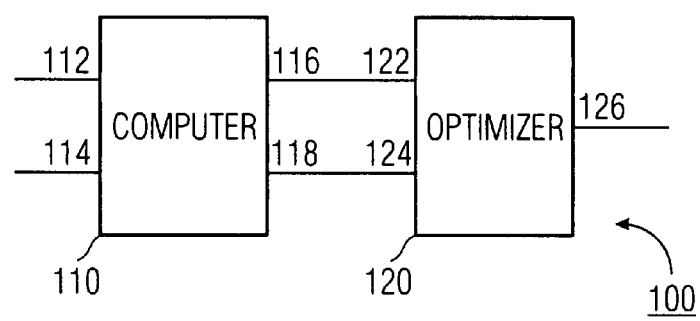
FIG. 1a) is a schematic representation of an inventive embodiment.

FIG. 1a depicts a schematized representation of an inventive embodiment, with an apparatus 100 for determining a spectral ratio between a first signal having a first spectrum which depends on a biological quantity, and a second signal having a second spectrum which depends on the biological quantity, the first signal and the second signal having a plurality of harmonics of a periodic signal. The apparatus for determining the spectral ratio comprises a computer 110 which receives the first signal at its first input 112, and receives the second signal at its input 114, and is configured for calculating a first wave ratio, output at a first output 116, between a first spectral value of the first spectrum which has a frequency of a harmonic of the plurality of harmonics, and a spectral value of the second spectrum which has the frequency of the harmonic. At its second output 118, computer 110 outputs a second wave ratio between a spectral value of the first spectrum which has a frequency of another harmonic of the plurality of harmonics, and a spectral value of the second spectrum which has the frequency of the other harmonic.

On its output side, computer 110 has an optimizer 120 connected downstream from it. The two outputs 116 and 118 of computer 110 are connected to two inputs 122 and 124 of optimizer 120. Optimizer 120 determines the spectral ratio while using the first and second wave ratios, the optimizer being configured to determine the spectral ratio such that it differs from the first and second wave ratios and meets an optimization criterion. The spectral ratio is then output at the output 126 of optimizer 120.

Figure 1B:
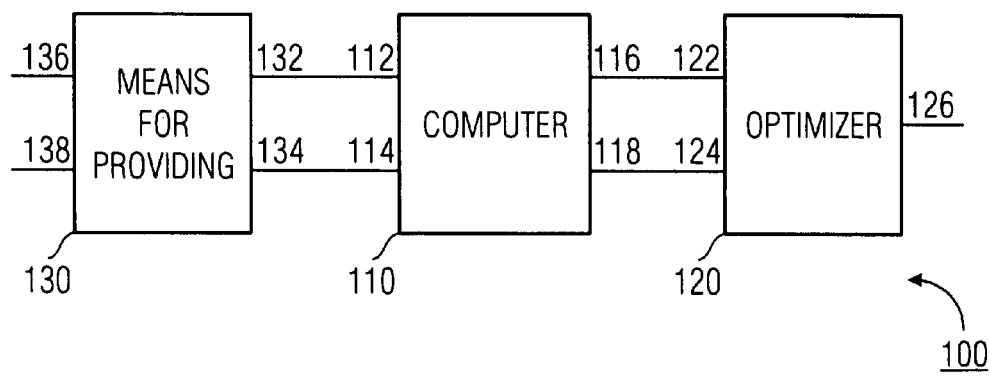
FIG. 1b) is a schematic representation of an inventive embodiment.

FIG. 1b shows an alternative schematic representation of the embodiment. FIG. 1b depicts the same components as FIG. 1a, the apparatus is extended by a means 130 for providing the two signals. Means 130 for providing the first signal having the first spectrum and the second signal having the second spectrum exhibits two outputs 132 and 134 connected to the two inputs 112 and 114 of the computer. Means 130 for providing the two signals also exhibits two inputs 136 and 138. At its inputs 136 and 138, means 130 receives two original signals having spectral components masked out therefrom, so that means 130 for providing the signals provides, at its outputs 132 and 134, signal portions of the original signals. At its inputs 112 and 114, respectively, computer 110 receives the two signals composed of signal portions of the original signals. For example, the original signals may be two optical receive signals detected in plethysmography which go back to light having different wavelengths (for example red and infrared light) and which have irrelevant spectral components masked out therefrom for determining, for example, an oxygen content in the blood.

In an inventive embodiment, a light source whose light is coupled into a part of a test person's body, and a signal received by a photodetector, is controlled such that it adopts, in a iterating sequence, the on state at irregular intervals. The irregularity causes an expansion to occur within the spectral range of the signal. The additional spectral components of the light signal give rise to additional interference immunity. In the simplest case, two spectral lines of the same level will arise. Since the probability that both spectral components will be interfered with at the same time is smaller than the probability that a single spectral component will be interfered with, a diversity gain arises in the frequency range. This diversity gain may be implemented by corresponding signal processing, so that increased interference immunity and, thus, increased reliability of the measurement of a physiological parameter is achieved by the irregular control of the light sources. In addition, a so-called spread gain results. By the irregular controlling, the energy of the useful signal is evenly distributed to several frequency portions. Since the irregularity is known, these energy portions may again be coherently overlaid within the receiver. Interference portions having the same frequencies are also overlaid within the receiver; however, since same are interdependent, a coherent overlay takes place here, so that a gain results for the useful signal. A narrow-band interferer which overlays the useful signal only at one frequency portion will experience, within the receiver, a spectral expansion which is analogous to that of the useful signal within the transmitter, since in both cases, signal portions are combined at irregular points in time.

Figure 2A:
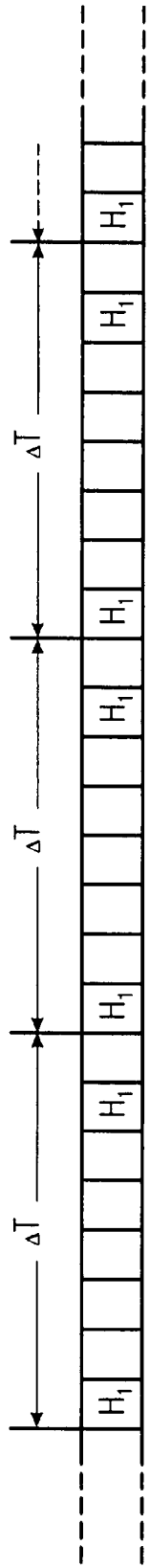
FIG. 2a) is a schematic representation of the irregular arrangement of the bright periods.
Figure 2B:
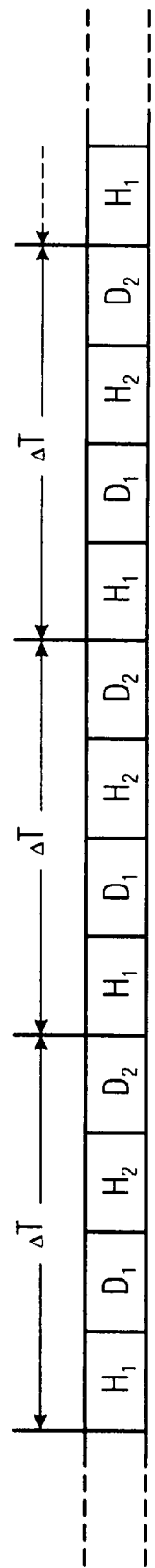
FIG. 2b) shows a regular arrangement of the bright periods in accordance with conventional pulse oximeters.

This irregularity of the bright periods is depicted in FIG. 2a in a schematized manner. FIG. 2a shows an iterating sequence of a duration of $\Delta T$. Within one sequence, a light source $H_1$ adopts an on state twice. This is indicated in FIG. 2a by the entries $H_1$. During the other moments, when no entries are present within the time raster in FIG. 2a, the light source is switched off. For comparison, FIG. 2b depicts a sequence of a conventional pulse oximeter. FIG. 2b shows a time division multiple access method (TDMA), wherein two light sources are controlled. During one sequence, each light source adopts the on state for one time slot. This is indicated by $H_1$ and $H_2$ in FIG. 2b. During the other time periods, depicted by $D_1$ and $D_2$ in FIG. 2b (D represents "DARK"), none of the two light sourced is to have adopted an on state.

Irregular controlling at the light source corresponds to a spread spectrum modulation. In combination with an adaptive filtering connected downstream, the spread spectrum modulation reduces signals portions which are to be attributed to ambient-light influences or electromagnetic interfering sources (e.g. high-frequency surgery), and such signal portions which are to be attributed to the subsampling. In addition, subsequent signal processing also enables a particularly efficient measurement of the oxygen saturation in the blood and of the heart frequency of a patient, it also being possible with the present method to perform reliable measurements even with a low arterial blood volume pulsation and while the patient is moving.

FIG. 3 shows an implementation of the embodiment. In FIG. 3, a spread spectrum modulation 300 is initially converted to an optical signal by an LED driver stage 305. In accordance with the spread spectrum modulation received, the LED driver means 305 couples light signals into a tissue 310 (e.g. into a finger), whereupon the light signals are modulated on their way through the tissue, and are subsequently received by a photoreceiver 315. Photoreceiver 315 converts the optical signals received to electrical signals and feeds same to an analog/digital conversion means 320 which converts the analog signal to a digital signal. The analog/digital conversion means 320 has a spread spectrum demodulator 325 connected downstream from it.

After the spread spectrum demodulation 325, the signal is adaptively filtered 330 and thereafter subject to a Fourier transformation 335. In a next inventive step, a reference spectrum is determined in that, in accordance with the invention, a spectral mask 340 is applied to the reference spectrum, whereupon the heart frequency of the test person may be established and will then be output at an output 345. In a next inventive analysis step, the so-called "complex total least squares fit" method 350, a variance of the difference of the different spectra which have been sized for light having different wavelengths may be determined, via a statistical analysis in the frequency range, and be output at the output 355 as a measure of reliability. Using the initial value provided by the inventive "complex total least squares fit" means 350, an associated oxygen content in the blood (SpO 2 value) may now be output, via a calibration function 360, at the output 365.

In order to be able to measure the light absorption of the tissue 310 with several light sources 305 having different wavelengths, and by means of a broad-band photoreceiver 315, a modulation method is necessitated, consisting of modulator 300 and demodulator 325. To better suppress interferences, the spread spectrum method is employed. This modulation method is based on the fact that because of the irregularity of the bright periods, the spectrum of the baseband signal is spread, or expanded. This effect is illustrated by FIGS. 4 to 9.

Figure 4:
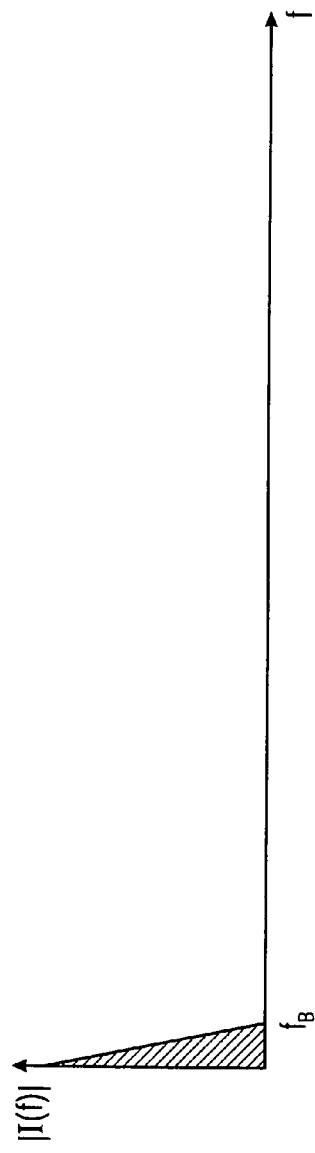
FIG. 4 is a schematized representation of a spectrum of a signal within the baseband.

Initially, FIG. 4 shows a spectrum |I(f)| of a baseband signal, the cutoff frequency of which is referred to as $f_B$. With conventional modulation methods, such as amplitude modulation, the spectrum of the baseband signal is shifted into a frequency range more suitable for the transmission.

Figure 5:
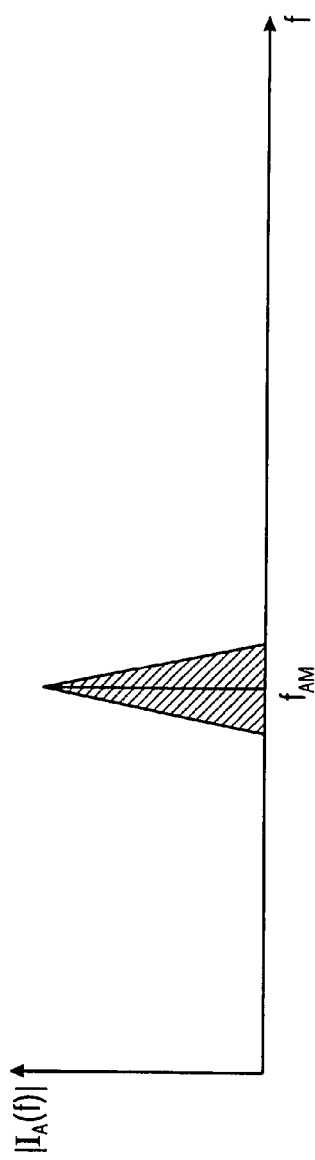
FIG. 5 is a schematized representation of a spectrum of a signal within the transmission band.

FIG. 5 illustrates this case, and depicts the shifted spectrum $|I_A(f)|$. Such a spectrum results when the baseband signal is multiplied by a higher carrier frequency. The spectrum of the baseband signal remains unchanged in terms of its shape and energy. If this signal is overlaid by an interferer, it will not be possible to suppress this interference by demodulation, i.e. by means of a shift-back from the transmission band into the baseband. In the case of the spread spectrum modulation, each transmit channel, which is understood to mean the transmit light signals of a wavelength, has a so-called chip sequence associated therewith which has been pre-computed. A chip sequence consists of a finite sequence of ones and zeros which are typically clocked in a frequency which is a hundred times higher than, by comparison, in a TDMA concept. The clock frequency is about 3 kHz.

From a mathematical point of view, the chip sequences must meet certain characteristics in order to achieve the desired spreading action of the interfering signal, and to enable the reconstruction of the plethysmograms as well as of the ambient-light channels. In principle, the chip sequences must be orthogonal to be able to implement a channel separation in the demodulation, and so that a demodulation without any cross-talk is enabled.

Figure 6:
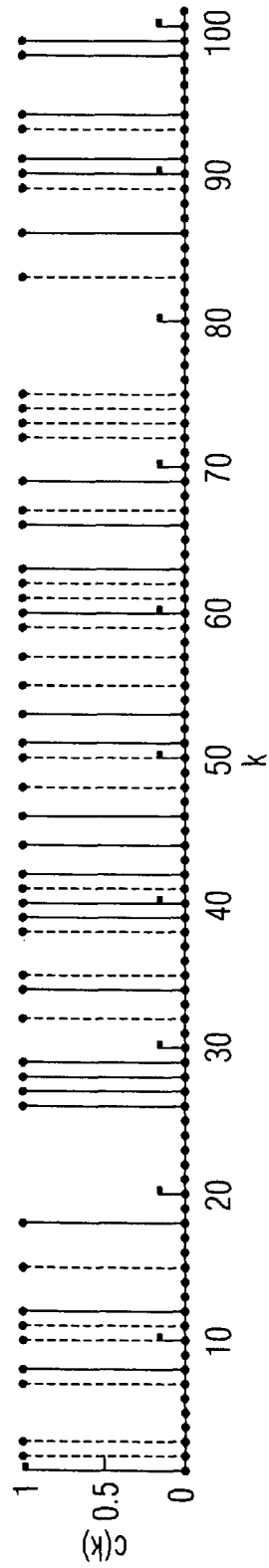
FIG. 6 is a schematic representation of two orthogonal chip sequences of a length of 101 chips.

FIG. 6 shows a schematic representation of two orthogonal chip sequences, the length of a chip sequence equaling 101 chips in the embodiment contemplated here. FIG. 6 depicts a time beam of a duration of 101 chip durations. The values of two chip sequences c(k) are plotted over these 101 chip durations. In the diagram, the two chip sequences are differentiated by dotted and solid lines, respectively. Whenever a chip sequence adopts a value of 1, this means that the light source associated is placed into the on state. It may be clearly seen in FIG. 6 that the two chip sequences are orthogonal, i.e. that the two associated light sources will never adopt the on state at the same time. In principle, it is also possible to employ chip sequences which simultaneously result in a 1, or it is possible to employ other sequences having other properties. Particular emphasis shall be placed on the property of the sequences which causes the individual bright periods to occur at irregular intervals, so that a spectral spread is achieved. In addition, it may be clearly seen in FIG. 6 that the individual bright periods within a sequence are arranged in an irregular manner, and that there are points in time when both chip sequences take on the value of 0, i.e. when both light sources are switched off in the implementation.

A further important property of the chip sequences is that their spectrum should be spread as evenly as possible, so that the signal energy will spread as evenly as possible to a frequency range as broad as possible.

Figure 7:
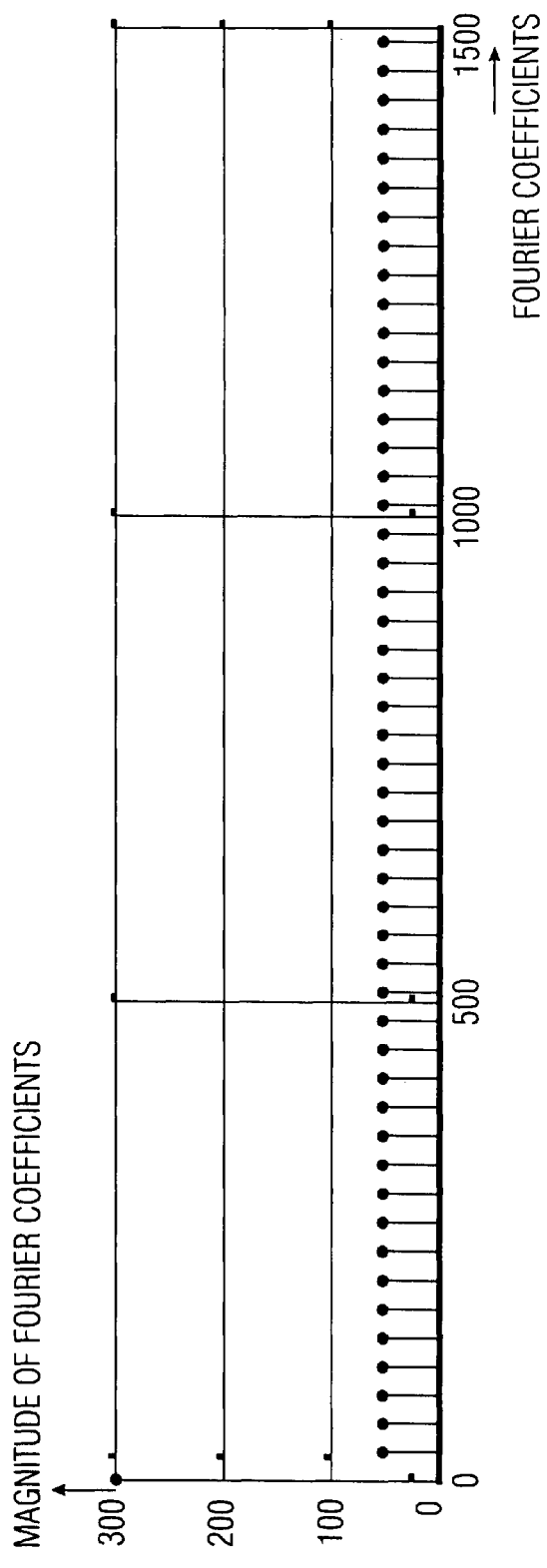
FIG. 7 is a schematic representation of a spectrum of a chip sequence of a length of 101 chips.

FIG. 7 shows the spectrum, i.e. the frequency range, of one of the chip sequences depicted in FIG. 6. It may be clearly seen in FIG. 7 that the spectrum of such a sequence is evenly spread, i.e. the spectrum is composed of equidistant identical values. The high direct component represented by the excessive value at the frequency of 0, may be explained in that the chip sequence can only adopt the values of 0 and 1. Thus, the sequence is not free from a mean value. The spectrum of a chip sequence may therefore be regarded as a "comb" of equidistant carriers of identical amplitudes. The spectral equipartition of a chip sequence results in that a narrow-band interferer will be spread, after demodulation, into a broadband noise. In the implementation of the embodiment is depicted in FIG. 3, the two LEDs are controlled using the chip sequences depicted in FIG. 6.

Figure 8:
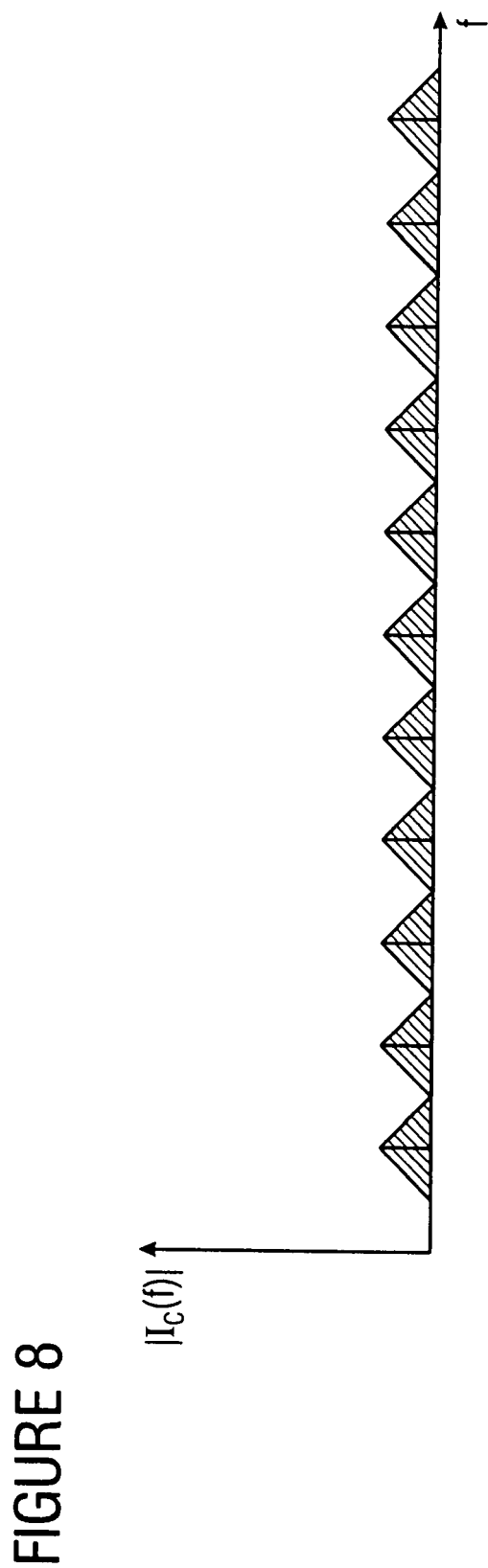
FIG. 8 is a schematic representation of the signal within the transmission band.
Figure 9:
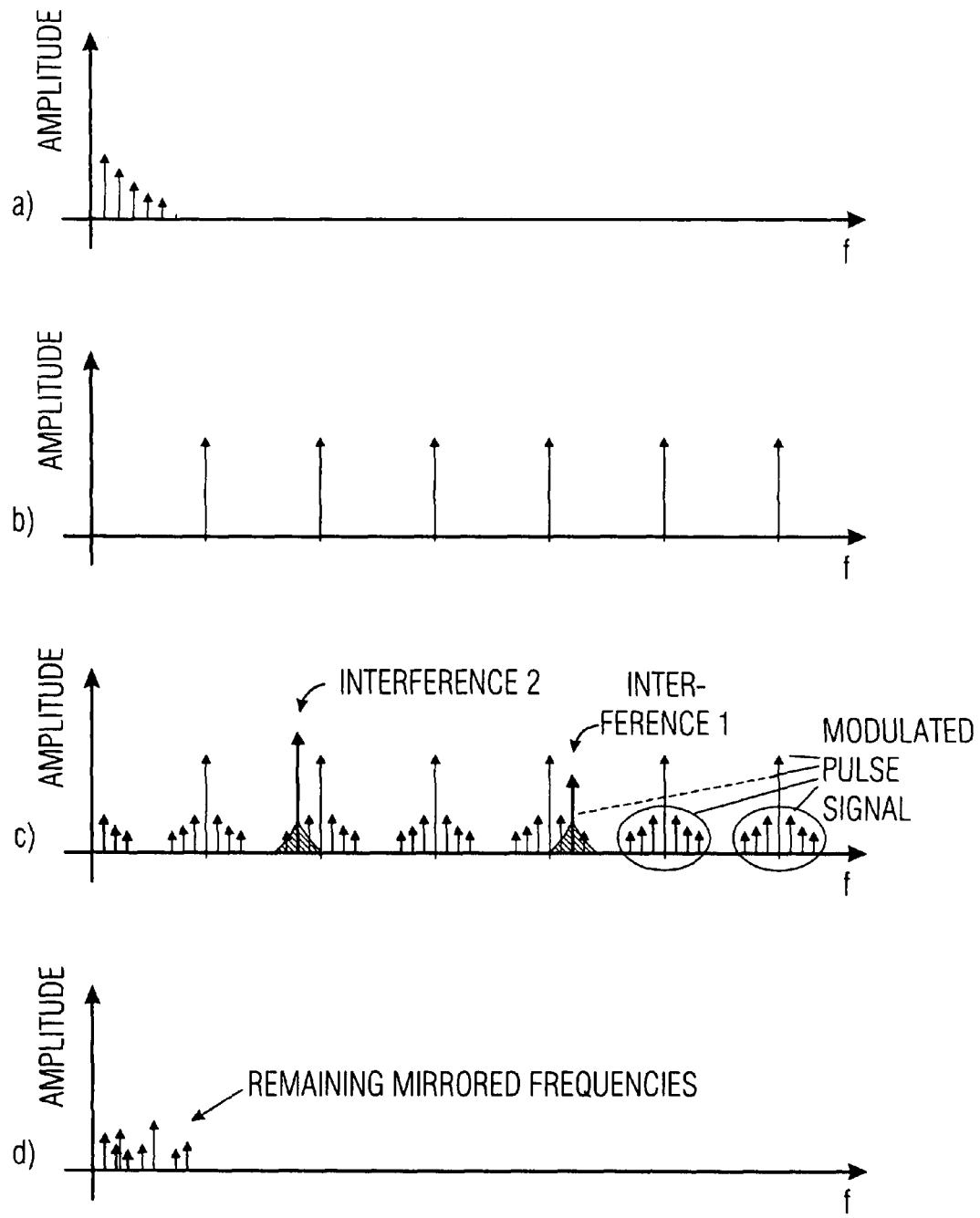
FIG. 9 is a schematic representation of the spread interference and de-spreading within the frequency range.

FIG. 8 shows the schematic representation of the signal of FIG. 4 within the transmission band $|I_C(f)|$. The baseband signal, as is depicted in FIG. 4, maintains its spectral shape, but its energy is distributed to many frequencies. This process is also referred to as spreading. If the signal depicted in FIG. 8 is interfered with by a narrow-band interferer, said interferer will be subject to spreading in the demodulation, whereas the energy portions of the signal of FIG. 8 will again overlay one another in a coherent manner within the baseband. Here, the demodulation corresponds to a renewed multiplication by the respective chip sequence. The result of the multiplication is then summed up across a length of chip sequences. Thus, if a receive signal is multiplied by one of the chip sequences, as are depicted in FIG. 6, it may easily be seen from FIG. 6 that by the multiplication, only those receive signals values are masked out from the receive signal which are received at a moment which correspond to a one in the respective chip sequence. These individual signal portions are then summed up across a chip sequence, as a result of which they will coherently, i.e. constructively, overlay one another. An interfering signal which has overlaid the receive signal is also masked in only at the respective moments in time. Also, the interfering signals are sampled at the respective moments in time and are summed up across the length of chip sequence. However, the interfering signals do not coherently overlay one another at the sampling moments, so that they will actually experience a spreading across the de-spreading, i.e. the multiplication by the chip sequence, so that after demodulation, these signals will be present in an attenuated form only.

FIGS. 9a)-d) depict the operation of the spreading once again within the frequency range. FIG. 9a) shows the spectrum of a signal within the baseband. FIG. 9b) shows the spectrum of a chip sequence, the spectrum ideally being evenly distributed in spectral terms. FIG. 9c) shows the spread baseband signal which now has energy portions at each individual frequency of the chip sequence. The energy of the baseband signal has been spread to the frequencies contained within the chip sequence. In the inventive implementation, the signal is received in this form from the tissue by the photosensor, the actual useful signal then was modulated to the spread signal through the tissue. FIG. 9c) further depicts two interferences, "interference 1" and "interference 2". The two interferences are narrow-band interferers as may be caused, e.g., by fluorescent lamps or high-frequency scalpels. FIG. 9d) shows the spectrum of the signal after demodulation, or after de-spreading. It may be seen that the baseband signal has been reconstructed, and that additional frequencies of the interfering signals within the baseband have been added. FIG. 9d) also shows that the remaining frequencies of the interference have clearly smaller amplitudes than the original interference itself, which is due to the spreading of the interfering signal.

Legendre sequences are chip sequences which meet the characteristics necessitated here and which exhibit good auto and cross-correlation characteristics. In the contemplated implementation of the embodiment, the sequences modulate two bright transmit channels and two dark transmit channels. The spectral properties of all sequences are identical and meet the equidistribution necessitated within the spectral range. In addition, a total of four sequences are considered, the four sequences being orthogonal to one another, which means that no two sequences will adopt the value of 1 at the same time. In principle, the use of other sequences is also feasible, the irregularity property of the bright periods is to be emphasized, this does not presuppose that at any moment in time, only one sequence may have a bright period. Two of the four sequences are used in an implementation of the embodiment to control two LEDs having different wavelengths (red and infrared), the two remaining sequences serve to detect ambient-light channels, they correspond to dark channels.

Figure 10:
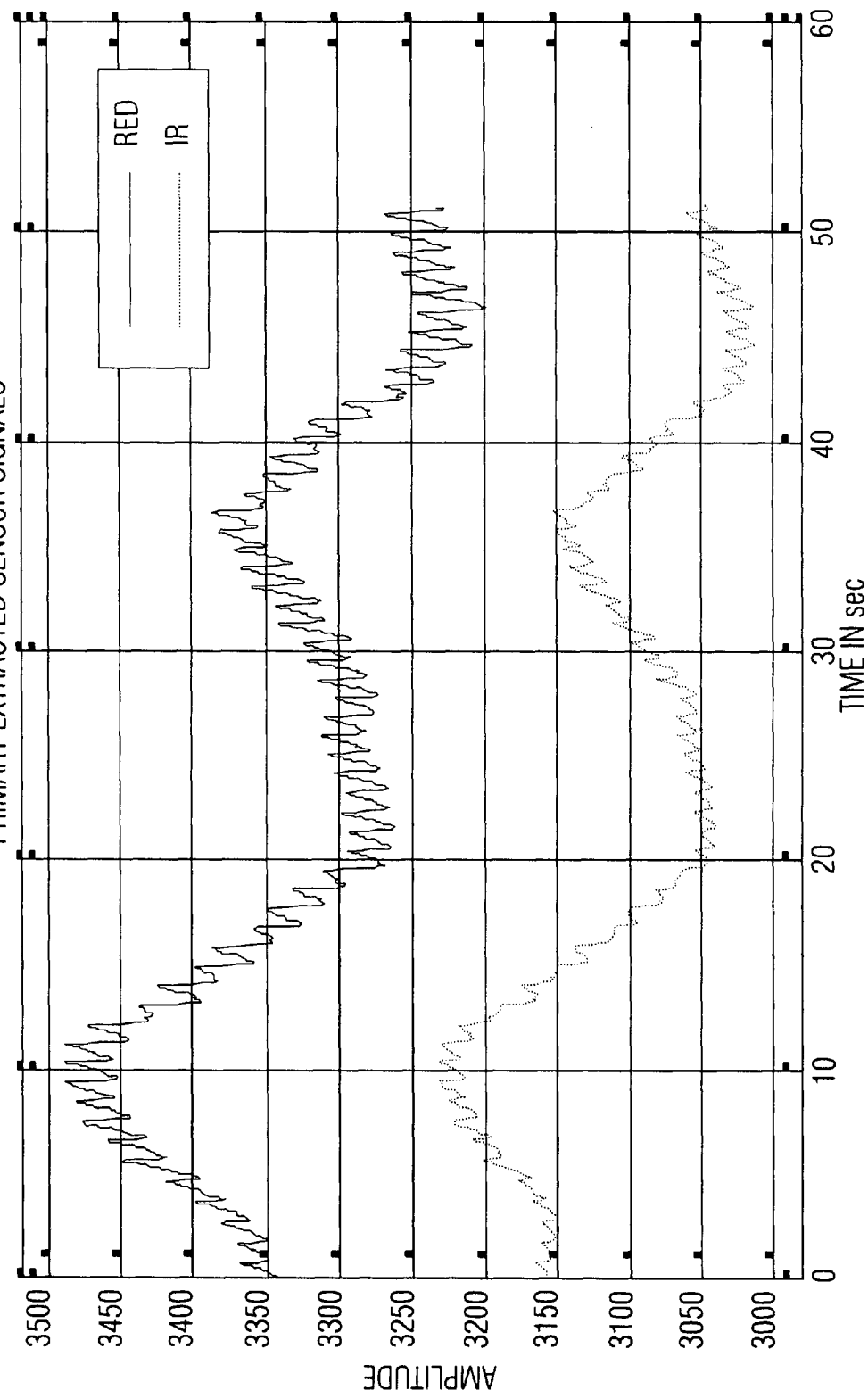
FIG. 10 shows two exemplary received waveforms of two LEDs having different wavelengths.

The LEDs are now controlled as monochromatic light sources via LED driver 305 of FIG. 3. The light of the LEDs which is modulated with the chip sequences passes through a tissue layer, and depending on the wavelength of the light source, it experiences an adequate attenuation in the process. The radiation of the LEDs, which is attenuated by the tissue, impinges at photoreceiver 315, is converted to a proportional photocurrent there, and is subsequently sampled, using an analog/digital converter 320, in a manner which is synchronous to the clock of modulator 300. The synchronicity between the modulator within the transmitter, and the AD converter and/or demodulator within the receiver may optionally be achieved by a control means which dictates clocks to both the transmitter and the receiver via control leads. The signal which has been synchronously sampled is fed to the spread spectrum demodulator 325. By means of the demodulation, spread spectrum demodulator 325 divides the signal of the photoreceiver up into individual channels. In a practically oriented implementation, these are two pulse channels for red and infrared LEDs, as well as two channels for measuring the ambient light. FIG. 10 shows two exemplary waveforms, the lower one corresponding to the red LED, and the upper one to the infrared LED. It may be seen in FIG. 10 that both signals are overlaid by a higher-frequency signal portion originating from the pulse signal of the test person, that both signals have a high direct component, and that both signals have a low-frequency interfering portion which may have been caused, for example, by changes in ambient light due to movements on the part of the test person.

Figure 11:
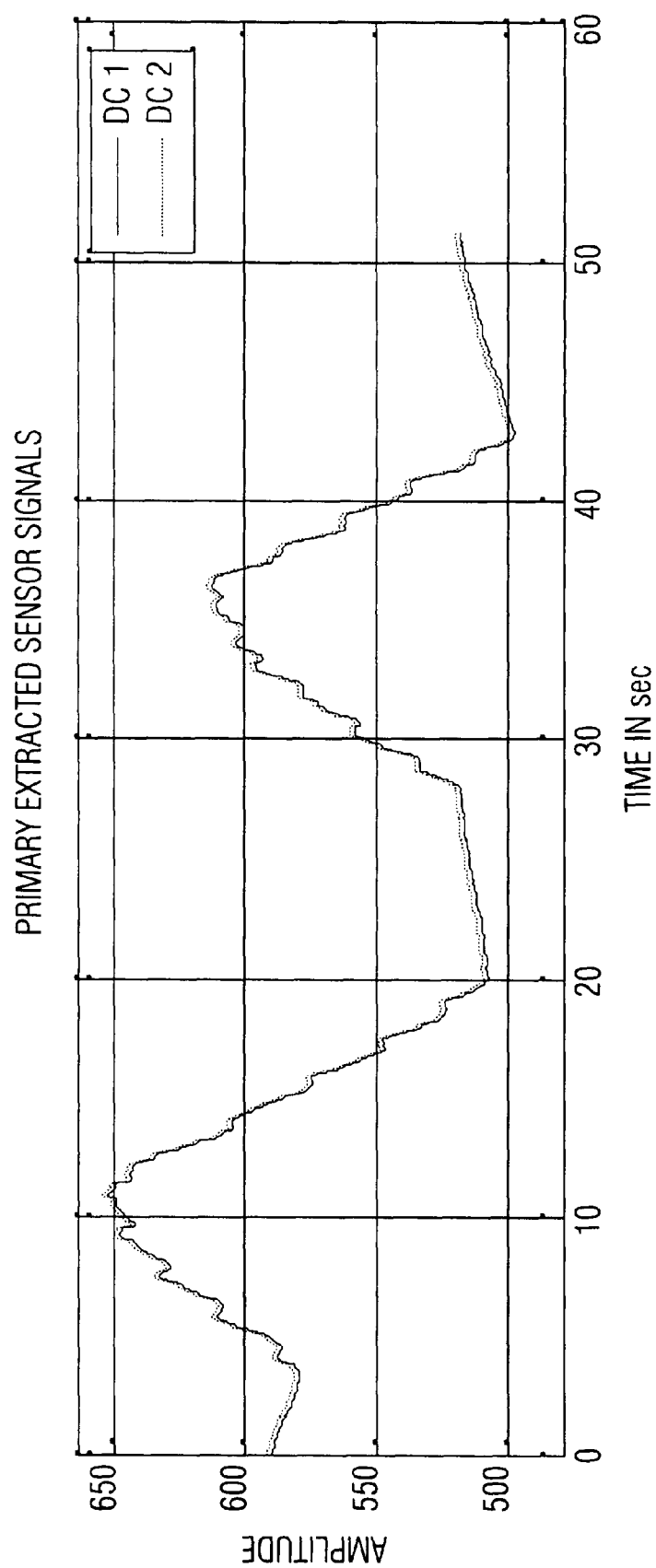
FIG. 11 is a representation of two exemplary waveforms for the dark duration and the ambient-light measurement, respectively.

FIG. 11 shows two exemplary waveforms for the two dark channels. In these two signals, too, it is possible to recognize the high-frequency portion originating from the pulse signal of the test person, as well as an interfering portion to be attributed to ambient-light changes. The direct component in FIG. 11 is correspondingly smaller than the direct component in FIG. 10, since both light sources are switched off during the dark channel phases. In order to specifically calculate, and extract, the influences of the ambient light from the bright transmit channels, the mean value of the two ambient-light channels is subtracted from the two bright transmit channels so as to remove that portion of ambient light which is below the two sampling frequencies from the signal measured. The formation of the mean value corresponds to the inventive formation of a weighted sum, as is implemented, in accordance with the invention, by a means 150 for forming a weighted sum in FIG. 1b).

For demodulation purposes, a so-called matched filter is used, for each chip sequence, for extracting the transmit channels from the receive signal. Such a matched filter is an implementation of the spread spectrum modulator 325 of FIG. 3 and may be described as a mathematical operation with a chip sequence. The sensor signal is cyclically multiplied by the chip sequence, and the result is summed up over one chip-sequence length in each case. In the realization of the embodiment which is described here, these are the respective Legendre sequences. Mathematically speaking, the matched filter implements a scalar product between the chip sequence and the receive vector, i.e. the sampled receive signal. Transmitter and receiver are synchronized. The scalar product leads to blockwise de-spreading of a transmit channel into the baseband. What results at the same time is a subsampling with a factor which corresponds to the length of the chip sequence for the useful signal. To avoid aliasing, the bandwidth of the signal must be reduced prior to each subsampling operation. Thus, an anti-aliasing filter is necessitated which may be integrated, along with the matched filter, into one filter.

Investigations have shown that interferences having large amplitudes are mainly due to artificial illumination. In Europe, the mains frequency is 50 Hz, the fundamental wave of the power (or of the intensity) is therefore 100 Hz, and its harmonic waves correspondingly amount to multiples of 100 Hz. Depending on the intensity of the interference, the attenuation of the extraction filter within the stop band is not sufficient. On the basis of these findings, the frequencies corresponding to a multiple of 100 Hz may be suppressed by adjusting the properties of the extraction filter (combined filter).

Figure 12:
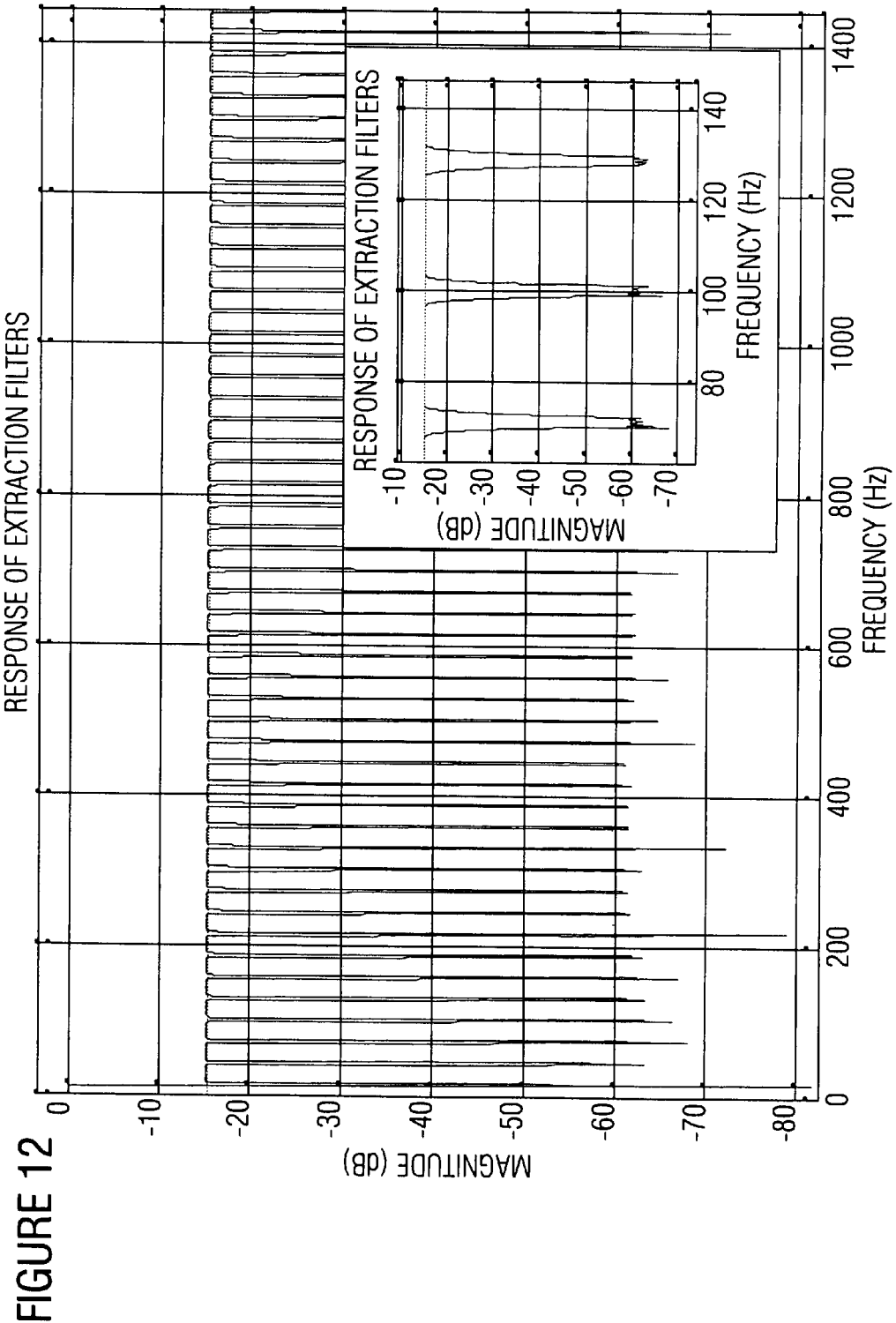
FIG. 12 depicts an exemplary transmission function of an extraction filter with an attenuation of 15 dB and a suppression of 100 Hz; enlargement in the area of 100 Hz.

By way of example, FIG. 12 shows a transmission function of an extraction filter with an attenuation of 15 dB, wherein, additionally, the interferers are suppressed at multiples of 100 Hz. Thus, the extraction filter already includes a low-pass filter necessary for subsampling, and at the same time a matched filter for de-spreading the spread signal from the transmission band into the baseband. A filter which implements subsampling is also referred to as a subsampler, the matched filter for de-spreading the spread signal is also referred to as a correlator, since it correlates a predefined chip sequence with the receive signal.

After extraction from the receive signal, the extracted and subsampled signals are present. The degree of subsampling is dependent on the length of the chip sequence. A sample of the useful signal results for each chip-sequence length due to the matched filter. By using several orthogonal chip sequences, several channels result during a chip-sequence duration, in the inventive embodiment, there are four channels, two bright transmit channels of the red and infrared LEDs, as well as two dark transmit channels, during which none of the transmit light sources adopts an on state, and which are used for ambient-light and interference compensation.

In addition, the interferences present above the useful band, i.e. interferences present above half the sampling frequency, are mirrored into the useful band at 15 dB by the extraction filter. The attenuation of the interferences above half the sampling frequency depends on the chip-sequence length. In the inventive realization of the embodiment, a chip-sequence length of 101 chips has been selected, which leads to an attenuation of 15 dB for interferences above half the sampling frequency. At the same time, the filter implements additional attenuation of all frequencies comprising a multiple of 100 Hz. FIG. 12 shows an exemplary transmission function of an extraction filter.

After the extraction filter, the useful signals are present within the baseband. To reduce the influence of the ambient light, in accordance with the invention, the ambient-light portion is subtracted from the useful signal, in accordance with the first means 110 for providing the time-discrete signal in FIG. 1b). In addition, a differential signal is generated for the adaptive filter 330 in accordance with the second means 120 for providing the first and second time-discrete reference signals, and with subtracting means 130, as depicted in FIGS. 1a) and 1b). For ambient-light subtraction, a mean value is initially formed from the dark channels, which is then subtracted from the bright transmit channels. Depending on the type of chip sequences used, and/or depending on the configuration of the spectra of the individual chip sequences, it may be advantageous not to determine the exact mean value of the dark channels, but to linearly weight the dark channels. In the implementation of the inventive embodiment, Legendre sequences of the length of 101 chips are used. This implementation results in an optimal weighting of the dark channels of from 47.5% to 52.5%.

For the purposes of further inventive signal processing, it is important to differentiate between two frequency bands into which an interferer may be categorized. On the one hand, the band exists below half the sampling frequency, the useful band. On the other hand, the band exists above this frequency, the transmission band. Frequency components which are due to interference and are categorized into the useful band may be removed from the two useful signals (bright transmit channels of the red and infrared LEDs) by means of dark-phase subtraction. The signals of these frequencies are equal both in phase and in amplitude, and therefore do not appear in the difference of the two dark channels, the differential signal. An interferer within the useful band (or the baseband) will thus continuously result in 0 for the differential signal. An interferer within the useful band could be a light source which is detected by the photosensor through the tissue, and the intensity of which is modulated with the changes in volume of the arterial blood. However, these portions are not to be filtered out from the useful signal, as they contain the information desired (the pulsatile portion).

By contrast, an interferer could be categorized into the transmission band. In this case, the attenuation of the extraction filter will set in, which initially causes the interference to fall into the useful band in an attenuated state. In the implementation of the embodiment, this attenuation amounts to 15 dB. In addition, signals of these frequencies are subject to a phase shift which is different for each channel. This effect is to be attributed to the sequential sampling; although the orthogonal chip sequences are interlaced, cf. FIG. 6, they realize the samples at different moments in time. For signals above half the sampling frequency, this leads to a phase shift of the subsampled signals in the individual channels.

Figure 13:
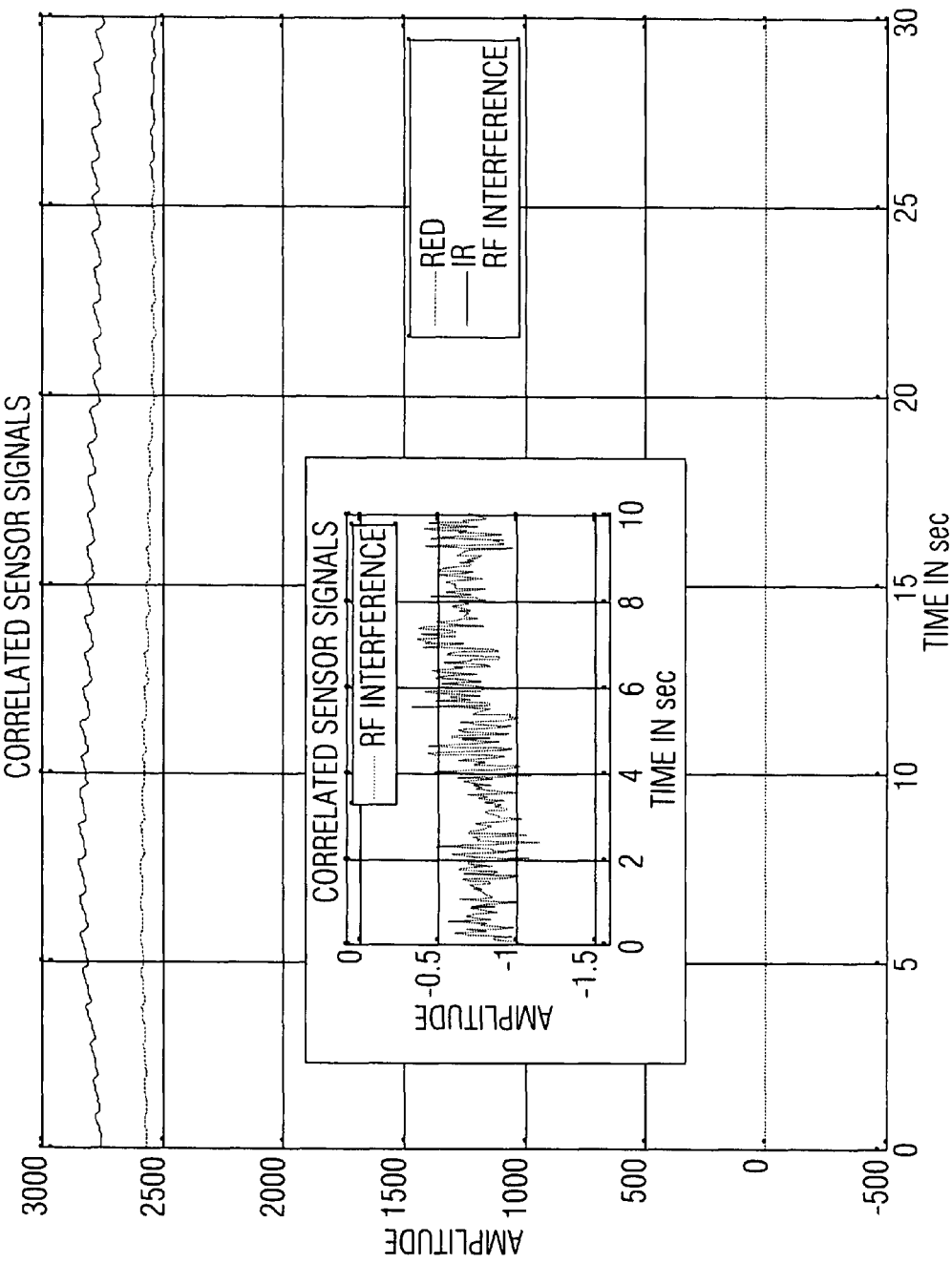
FIG. 13 depicts exemplary waveforms of the bright transmit channels from which the ambient-light signal has been subtracted, the enlargement shows the reference signal.

Thus, the difference between the two dark transmit channels (the differential signal) does not result in an extinction of these signals, but results in a signal, the frequency components of which contain the mirrored frequencies of the interferer from the transmission band. This signal now serves as a differential signal for an inventive adaptive filter 330, so as to reduce the remaining interferences from the transmission band as well. The ambient-light subtraction thus removes the interferences from the useful band, but also contains phase-shifted interfering portions from the transmission band. Once the interferences from the transmission band have experienced attenuation by the extraction, portions of this interference are now re-fed to the useful signal by the ambient-light subtraction. Therefore, what results is not the full attenuation for the interfering signals from the transmission band, but a smaller value. In the implementation of the inventive embodiment, the attenuation of the extraction filter initially amounts to 15 dB, but is reduced again by 3 dB by the ambient-light subtraction, so that a total attenuation of 12 dB results for interferers from the transmission band. FIG. 13 shows two exemplary waveforms for the two transmit channels, red and infrared LEDs, from which the ambient-light signal has been subtracted. In addition, FIG. 13 shows an exemplary differential signal in a magnified form.

Figure 14:
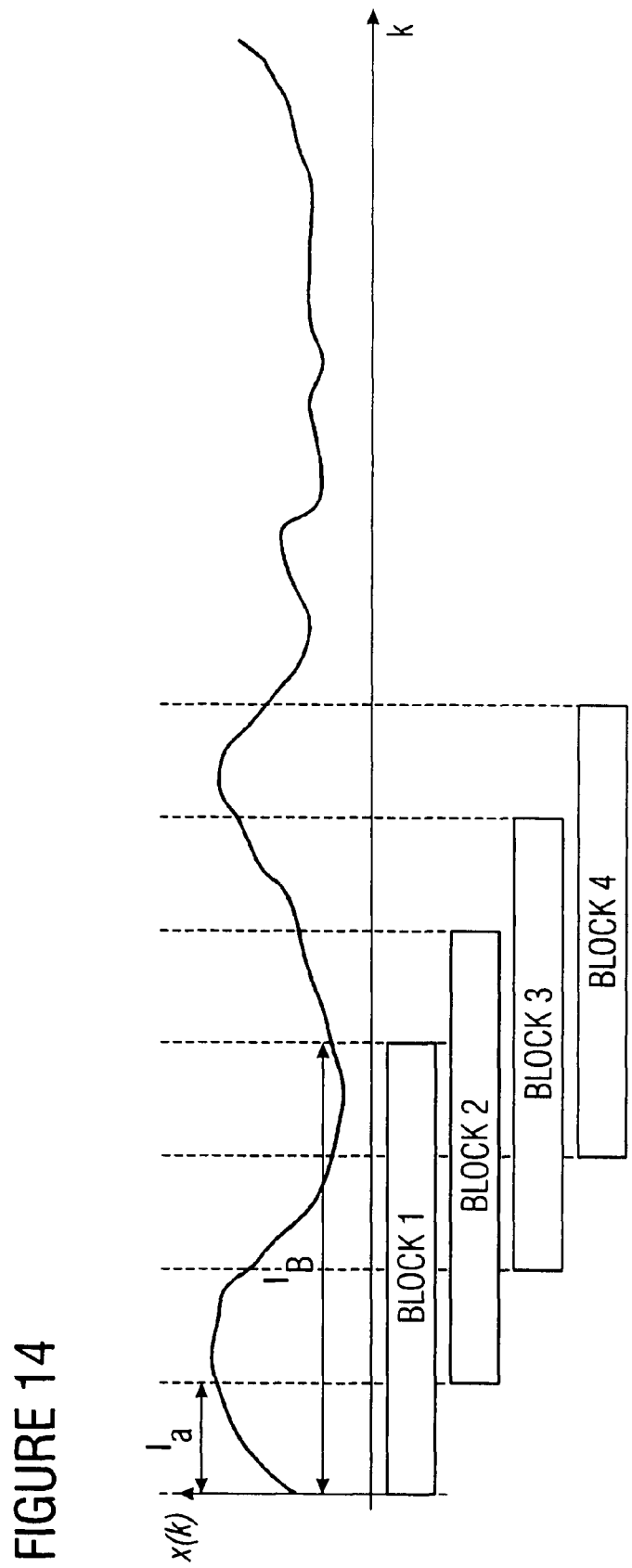
FIG. 14 is a schematic representation of the block formation for further signal processing, $l_B$ corresponds to the block length, $l_a$ is a measure of the overlap.

For further signal processing, a block formation for the individual signals initially occurs. For this purpose, the signals are divided up into blocks of equal lengths, the individual blocks overlapping. FIG. 14 illustrates the block formation for further signal processing. Blocks of a length of $l_B$ are formed from the samples of a useful signal, a new block being formed every $l_a$ samples.

The useful signals are subsequently fed to a frequency-separating means. It is the task of the frequency-separating means to filter the direct component and the pulsatile portion from the input signals. In the implementation of the inventive embodiment, the separating frequency of the frequency-separating means amounts to about 0.5 Hz. FIG. 15a) shows the exemplary curve of an input signal being fed to the frequency-separating means. In addition, FIG. 15a) depicts the low-pass filtered portion (DC portion) of the input signal. FIG. 15b) depicts the associated high-pass portion (AC portion) of the input signal. Further signal processing only relates to the high-pass portion of the input signal.

The high-pass filtered useful signals are now fed to an adaptive filter 330. It is the task of the filter, also referred to as interference canceller, to reduce interferences which were present in the transmission band and were mirrored, after demodulation, into the useful band in an attenuated state, cf. FIG. 9d). The differential signal which contains the frequencies of the interference in the useful band has been formed by subtraction from the dark transmit channels. The differential signal differs in phase and amplitude from the interferences overlaid on the useful signals. The phase difference is caused by the sampling offset in time, the difference in amplitude is caused both by the sampling which is offset in time, and by the subtraction. It is therefore the task of the adaptive filter to filter out the undesired image frequencies from the useful signals using the differential signal. For this purpose, an interfering signal is constructed, from the differential signal, which is as close as possible to the interference overlaid upon the useful signal. There are several mathematical methods of determining the coefficients for adaptive filter 330. One known method would be to select the coefficients of adaptive filter 330 such that the deviation between the differential signal and the useful signal is minimized. For determining the coefficients, the complex total least squares fit method is also to be mentioned here.

Figure 16:
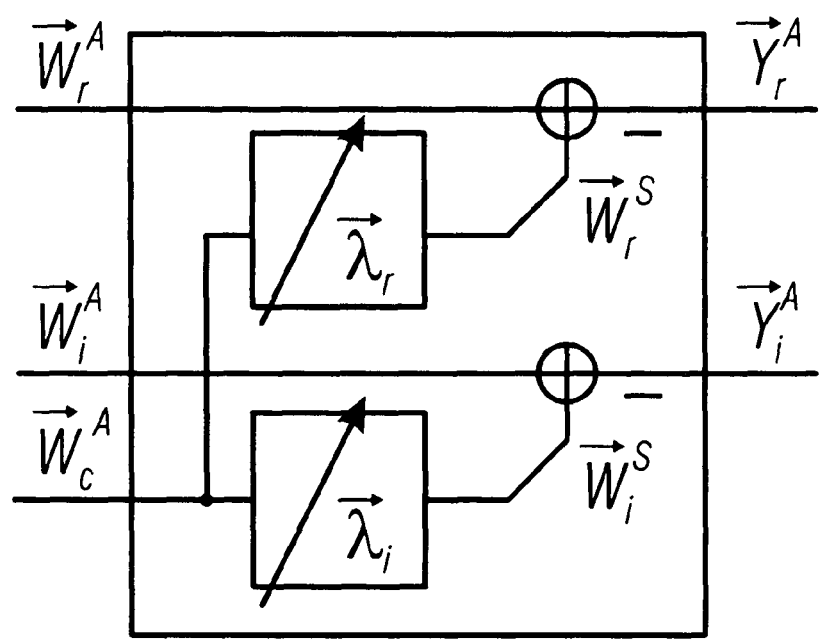
FIG. 16 depicts a model of the adaptive filter, with the input quantities on the left and the output quantities on the right, the reference signal being designated by $W^A_c$.

FIG. 16 shows the model of the adaptive filter with the time-discrete input quantities $\vec{w}_r^A$ and $\vec{w}_i^A$ for the two input signals of the bright transmit channels for red and infrared, A here indicating that the input signals are high-pass filtered. In principle, the operations described below are applied to both input quantities separately, since the interference contemplated is present in them in a phase-shifted manner. The differential signal is also high-pass filtered as a matrix $W_c^A$, and forms the basis for determining the adaptive filter coefficients $\vec{\lambda}_r$ and $\vec{\lambda}_i$. Matrix $W_c^A$ results from blocks of the differential signal which are high-pass filtered to remove the direct component. The columns of the matrix each form a block of samples, e.g. of a length of 256. This block is indented in the matrix on a column-by-column basis, by one sample each, the matrix has as many columns as there are coefficients for the adaptive filter. The matrix may be described as $$[W_c^A]_{ij}(k) = w_c^A(i + k \cdot l_a + j) \quad (1)$$
$$\forall j \in \{0, 1, \ldots, N_{ifc}\}$$
$$\forall i \in \{0, 1, \ldots, l_B - 1\},$$

wherein $w_c^A$ represents the high-pass filtered elements of the differential signal, k is a discrete control variable of the block formation, $l_a$ is the jump constant in the block formation, $l_B$ is the block length, and $N_{ifc}$ is the filter arrangement, i.e. the number of filter coefficients of the adaptive filter, or interference canceller, reduced by one. The output of the adaptive filter thus is a weighted sum of blocks of the differential signals, the blocks having been shifted by one sample each. Using the adaptive filter, the interference vectors are initially reconstructed, which are designated by $\vec{w}_r^s$ and $\vec{w}_i^s$ in FIG. 16 and overlaid on input signals $\vec{w}_r^A$ and $\vec{w}_i^A$. By means of subtraction, the interference effects in the input signals $\vec{w}_r^A$ and $\vec{w}_i^A$ are reduced, as is depicted in FIG. 16.

What is initially sought for is a linear combination $\vec{\lambda}$ of basis $W_c^A$ which best reproduces the input signal, i.e. a reconstruction of the interference has been overlaid on an input signal $\vec{w}^A$.

$$\vec{w}^A \overset{!}{=} W_c^A \vec{\lambda}. \quad (2)$$

There are more equations than unknown variables, in that one assumes that the adaptive filter comprises fewer coefficients than the block length to be processed. This is why there is no specific solution in this case. What is sought for is a vector $\vec{\lambda}$ which best fits the over-determined equation system:

$$\|W_c^A \vec{\lambda} - \vec{w}^A\| \to \text{Minimum}. \quad (3)$$

This problem may be addressed using the pseudo inverse. Thus, using vector $\vec{\lambda}$, one obtains a linear combination of $W_c^A$ which may be used to describe the interference.

$$(W_c^A)^\# \vec{w}^A = \vec{\lambda}. \quad (4)$$

Thus, the interferer may be reconstructed on the basis of the input signal:

$$\vec{w}^s = W_c^A (W_c^A)^\# \vec{w}^A. \quad (5)$$

It may also be seen from FIG. 16 that the difference between the estimated interferer and the input signal results in the filtered signal:

$$\vec{y}^A = \vec{w}^A - \vec{w}^s, \quad (6)$$

or $$\vec{y}^A = \vec{w}^A - W_c^A (W_c^A)^\# \vec{w}^A = \vec{w}^A (E - W_c^A (W_c^A)^\#), \quad (7)$$

wherein E represents an identity matrix. An alternative implementation of the present invention would be a filter which implements a notch filter on the basis of the knowledge of the frequencies occurring in the differential signal, which is switched into the path of the useful signal, and which attenuates the frequencies of the differential signal.

Figure 17:
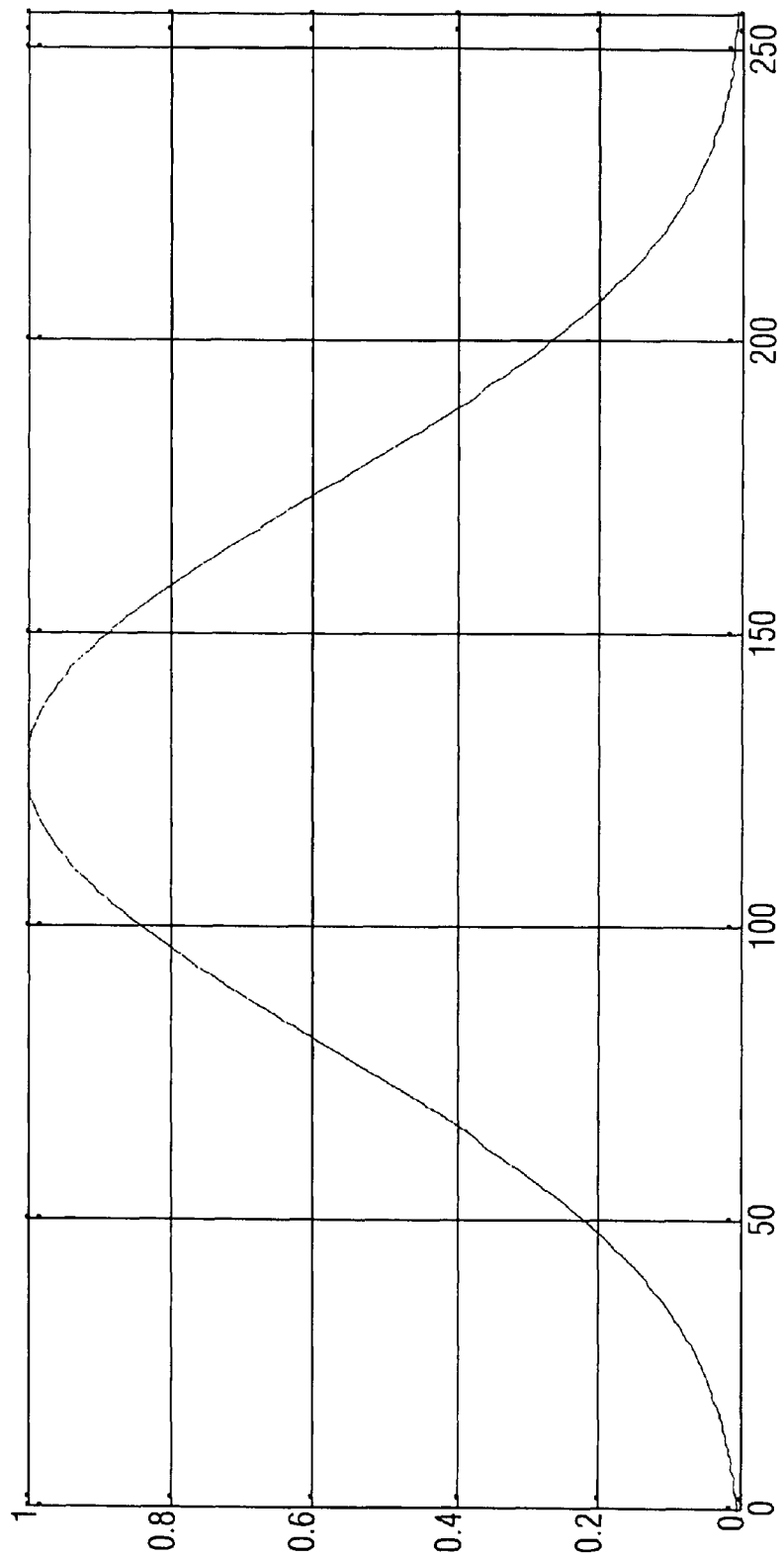
FIG. 17 depicts an exemplary curve of a Kaiser-Bessel window having a block length of 256 points.

Since examinations are subsequently performed in the frequency range, the input signals are transformed into the frequency range by means of Fourier transformation. Due to the block formation, unwanted side effects result in the frequency range. A block formation is to be equated with a multiplication of a rectangular pulse, which masks out the very block under consideration from a receive signal, by the receive signal itself. If this block is subject to Fourier transformation, one will obtain, in the frequency range, a convolution of the Fourier-transformed rectangular pulse (since function) with the actual spectrum of the sequence of receive signal samples. To reduce the unfavorable effects caused by the convolution with the sinc function in the frequency range, the block of receive signal samples is multiplied, in the time domain, by a window function having a narrower spectrum than the sinc function. For implementing the embodiment, a Kaiser-Bessel function is used for this purpose. FIG. 17 depicts the waveform of a Kaiser-Bessel window by way of example. Multiplication of the signal blocks by the window function may optionally also be performed prior to the adaptive filtering.

Figure 18:
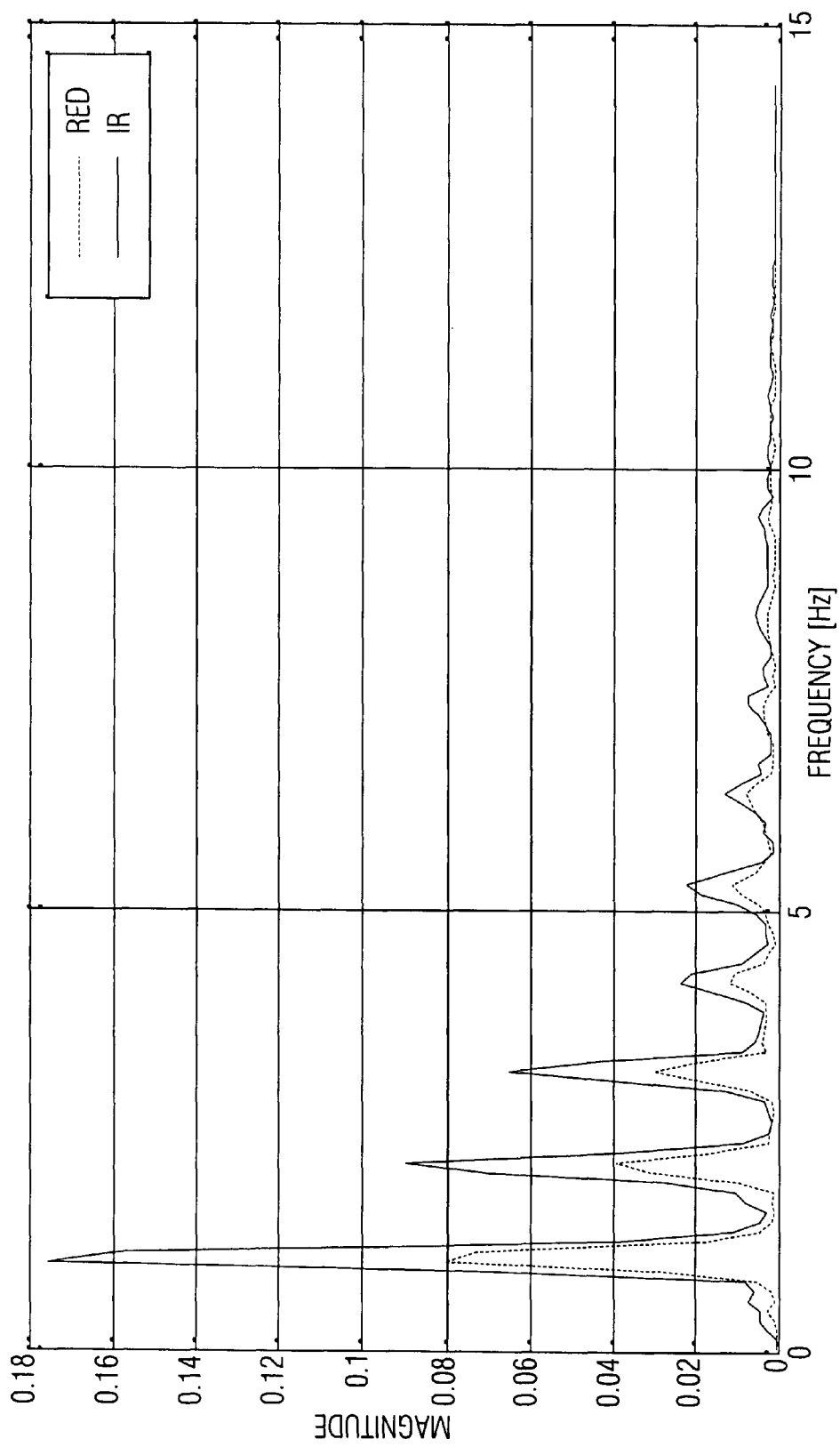
FIG. 18 is an exemplary spectral curve of the normalized useful signals for the two bright transmit channels, red and infrared.

For further signal processing, the two useful signals are now normalized. Subsequently, the Fourier transformation is conducted. After the Fourier transformation, the spectra may be presented in different views, such as their curve as a function of time or as a function of the frequency. FIG. 18 shows exemplary spectra of the normalized signals from the bright transmit channels red and infrared. The spectra show signals under good conditions, i.e. with relatively little interference. The Fourier transformation 335 is followed, in a next signal processing step, by determining, in accordance with the invention, the reference spectrum, and by applying the inventive spectral mask 340 for determining the heart frequency.

In accordance with the invention, a reference spectrum is determined from the two spectra having been determined from the two bright transmit channels. In this embodiment, after the Fourier transformation there will be two spectra whose time signals without the influence of interference would be perfectly correlated with one another, and whose spectra would be linearly dependent. Here, the spectra are described as vectors, and in a case of non-interference, a spectrum could be expressed as a linear combination of the other:

$$\vec{\gamma}_r \stackrel{!}{=} \rho \vec{\gamma}_i. \tag{8}$$

$\vec{\gamma}_r$ corresponds to the red bright transmit channel, $\rho$ corresponds to the linear coefficient, and $\vec{\gamma}_i$ corresponds to the infrared bright transmit channel. Since both spectra are interfered with, the resulting equation system is over-determined and cannot be solved. If the equation could be solved, i.e. if no interference was present, then the scalar quantity $\rho$ would already be the ratio by means of which the desired $SpO_2$ value could be determined via the calibration function. Since equation (8) cannot be solved, what is now sought for is a $\rho$ which, in accordance with the invention, best fits the equation. This problem may be illustrated by plotting the two spectra in an x-y plot.

Figure 19:
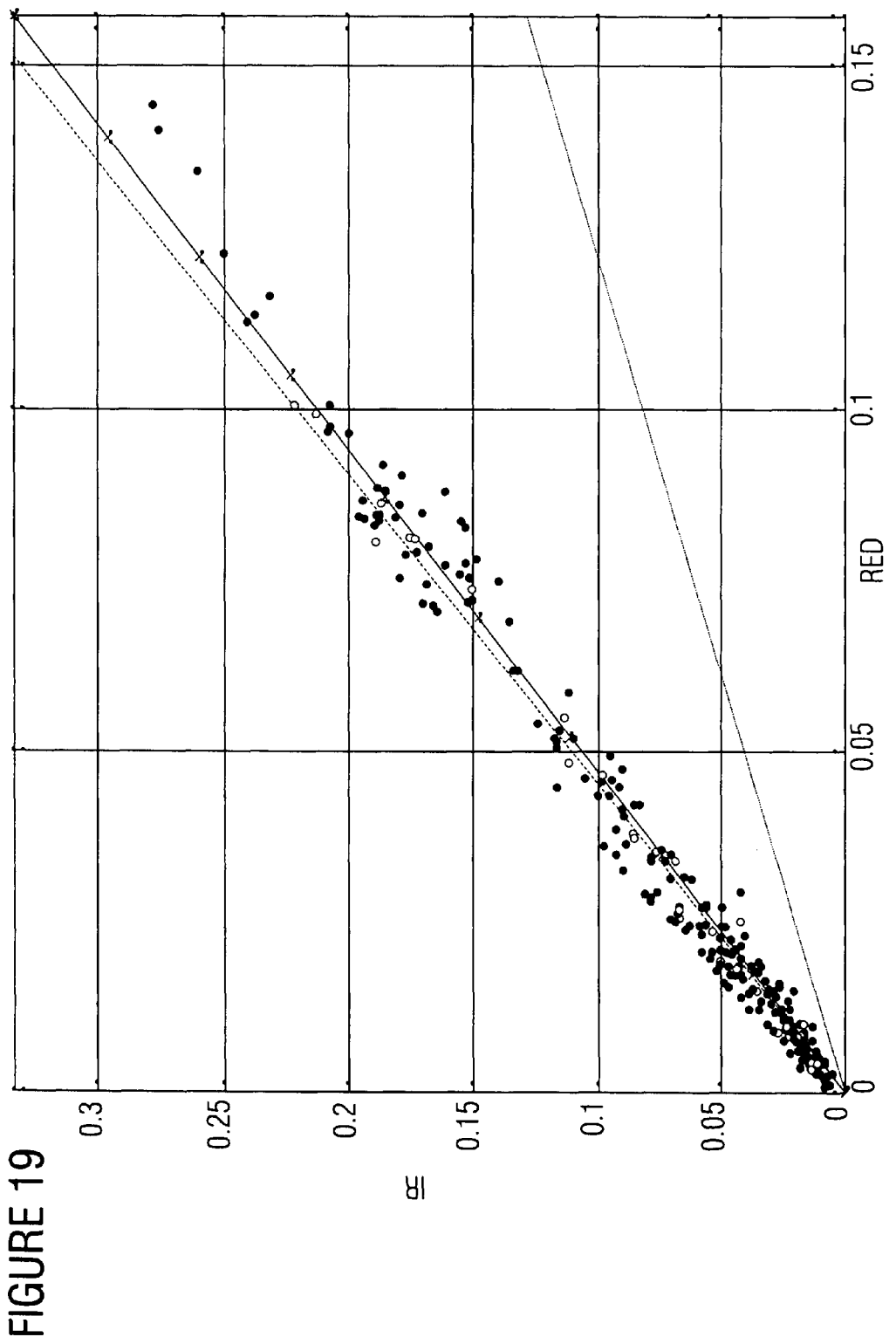
FIG. 19 is an exemplary representation of the two spectra for red and infrared transmit channels, spectral values of identical frequencies being plotted against one another.

FIG. 19 illustrates such an x-y plot. Due to interference, the spectra are different. If the spectra were identical, the dots in FIG. 19 would result in a perfect original straight line. But since the spectra are interfered with, the dots plotted in FIG. 19 form a cloud through which several straight lines may pass.

In addition, FIG. 19 has a straight line 1900 drawn therein which limits the range of values of the occurring slopes toward the downward end. Straight line 1900 corresponds to a blood oxygen saturation of 70%, the straight line 1910 corresponds to a blood oxygen saturation of 100%. Straight line 1920 is that straight line which has been determined using the inventive method, the determination of its slope will be described in detail below. What is sought for is a linear combination having a linear coefficient $\rho$ which best meets equation (8). Equation (8) is expanded by two interference vectors $\vec{i}_r$ and $\vec{i}_i$, since due to interferences, such as motion artifacts or white noise, two different interfering signals have been additively overlaid on each channel. The spectra may be decomposed into a pure non-interference pulse signal portion ($\vec{\gamma}_{r,p}$, $\vec{\gamma}_{i,p}$) and an additive interference portion ($\vec{i}_{r,p}$, $\vec{i}_{i,p}$), $$\vec{\gamma}_r = \vec{\gamma}_{r,p} + \vec{i}_r, \text{ and } \vec{\gamma}_i = \vec{\gamma}_{i,p} + \vec{i}_i. \tag{9}$$

The over-determined equation system then reads:

$$\vec{i}_r + \vec{\gamma}_{r,p} \stackrel{!}{=} \rho(\vec{\gamma}_{i,p} + \vec{i}_i). \tag{10}$$

Figure 20B:
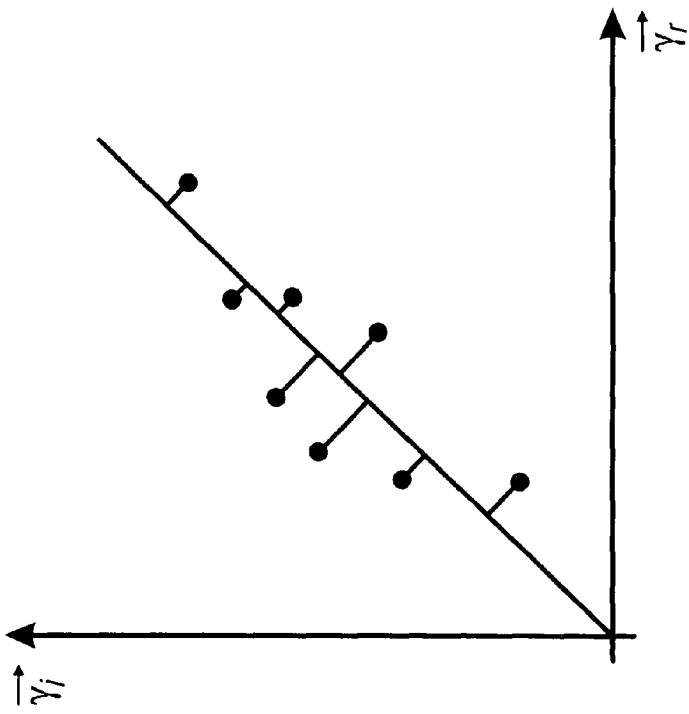
FIG. 20b) is a schematic representation of the total least squares fit method for minimizing the actual distances from a straight line.
Figure 20A:
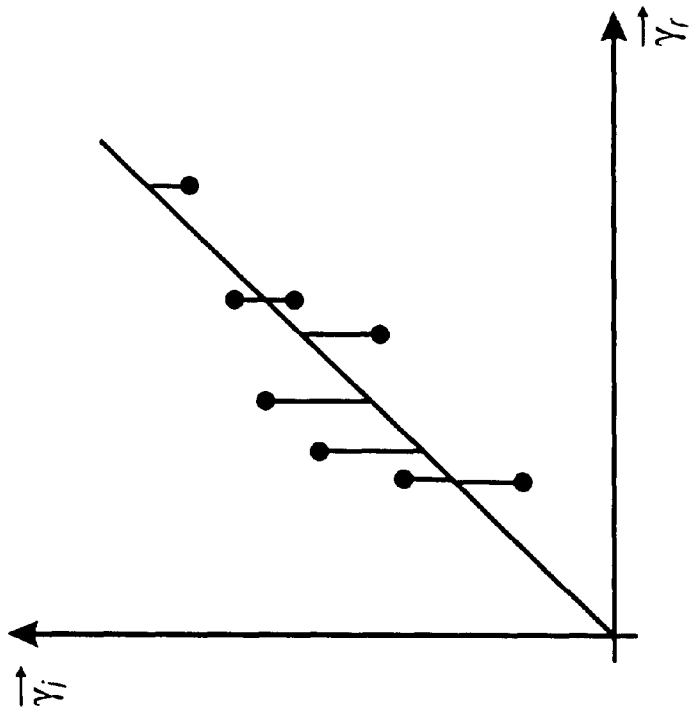
FIG. 20a) is a schematic representation of the least squares fit method for minimizing a vertical distance from a straight line.

The problem cannot be solved using the method of the least squares fit, since this would only be possible if only one of the two signals had been overlaid with interferences. In comparison, FIG. 20a depicts the least squares fit method, which corresponds to a minimization of a vertical distance, and FIG. 20b depicts the total least squares fit method, which corresponds to the minimization of the actual distance from the straight line to be determined. In both cases, one attempts to minimize the sum of the squares of the drawn-in distances between the respective dots and a straight line, dots located further from the origin being more heavily weighted, which is also desired in the present embodiment. Coefficients as correspond, for example, to the fundamental wave of a pulse signal, are more highly evaluated than coefficients of the relatively less intense harmonics. The slope of the straight line in both cases is the ratio $\rho$, however, the total least squares fit method is a better approximation, since it is only here that the actual distance from the points is taken into account. For solving the problem in accordance with equation (10), a singular-value decomposition is employed, by means of which a total least squares fit method may be performed. The singular-value decomposition is based on decomposing any matrix A into three matrixes:

$$A = U\Sigma V^+. \tag{11}$$

The product of the three matrixes of the singular-value decomposition again yields matrix A. It is specifically matrix $\Sigma$ that is of importance to the embodiment presented here. The diagonal elements of matrix $\Sigma$ are referred to as singular values. For further investigation, a matrix A is composed of the two column vectors, both of which represent the spectrum of the undisturbed signals with their additive interferers:

$$A = [\vec{\gamma}_r, \vec{\gamma}_i] \in C^{128 \times 2}. \tag{12}$$

It is very likely that the rank of this matrix equals 2, since it is absolutely unlikely, due to the additive interferers, that the column vectors are linearly dependent. By means of singular-value decomposition, it is possible, on the one hand, to determine the rank of the matrix, but on the other hand it is also possible to examine how close a matrix is to the lower rank. A matrix may be found which is as similar as possible to matrix A and the rank of which is lower than that of matrix A. If the rank of matrix A could be reduced to 1, the column vectors would become linearly dependent, and the spectra would be identical except for factor $\rho$. One of the spectra created in this manner could then be used, in accordance with the invention, for further calculation, since from then on it would carry the information of both channels.

If a singular-value decomposition is performed for A, one will obtain, for $\Sigma$, a matrix of the form:

$$\Sigma = \begin{bmatrix} \Sigma_1 & 0 \\ 0 & \Sigma_2 \end{bmatrix}. \tag{13}$$

The rank of a matrix A corresponds to the number of all singular values which are different from zero. Since the rank of matrix A equals 2, both singular values will be larger than zero, also $$\Sigma_1 \geq \Sigma_2 > 0. \quad (14)$$

Element $\Sigma_2$ reveals how close matrix $\Sigma$ is to the next rank down, i.e. in the present embodiment, how close matrix $\Sigma$ is to rank 1. What follows therefrom is that the size of $\Sigma_2$ is a function of the intensity of the overlaid interferences which are overlaid on both spectra and are independent of one another. The rank of matrix A may now be reduced to 1 in that $\Sigma_2$ is set to zero. Independent interferences overlaid on both spectra may be clearly reduced in this manner. Dependent interferences, i.e. interferences which in both signals are the same or are linearly dependent on one another, will initially remain within the two spectra. Reconstruction of matrix $\vec{A}$ results in a new matrix having a rank of 1:

$$\tilde{A} = U \begin{bmatrix} \Sigma_1 & 0 \\ 0 & 0 \end{bmatrix} V^+. \quad (15)$$

What results is a matrix, the column vectors of which are linearly dependent, and which results from applying the total least squares fit method to the two column vectors of matrix A which are overlaid by interferences. The two column vectors are complex spectra and represent, at the same time, the best approximation to the spectra overlaid by interferences. In accordance with the invention, the two spectra could also be determined in accordance with another optimization criterion, such as the least squares fit method. The independent interferences, such as, for example, adaptive white noise, have been removed from the linearly dependent spectra of matrix $\vec{A}$ in the manner described, matrix $\vec{A}$ now results as $$\vec{\tilde{A}} = [\vec{\gamma}_{r,f} \vec{\gamma}_{i,f}] \in C^{128 \times 2}. \quad (16)$$

With the column vectors thus determined, a solvable equation system results for the ratio $\rho$ for computing the oxygen saturation, $$\vec{\gamma}_{r,f} = \rho \vec{\gamma}_{i,f}. \quad (17)$$

However, the ratio $\rho$ is not used yet at this point, since if a linearly dependent interference having a high amplitude has identically overlaid on the two spectra, this interference cannot be reduced by means of the method proposed here. To filter out this type of interference from the spectrum determined, the step of spectral mask 340 is used for determining a biological quantity, such as the heart frequency. As the basis for calculation, the step of the spectral mask 340 necessitates the reference spectrum, which is representative for both channels. Since the two spectra of equation 16 are linearly dependent on one another, each of the two spectra represents both bright transmit channels.

Figure 21A:
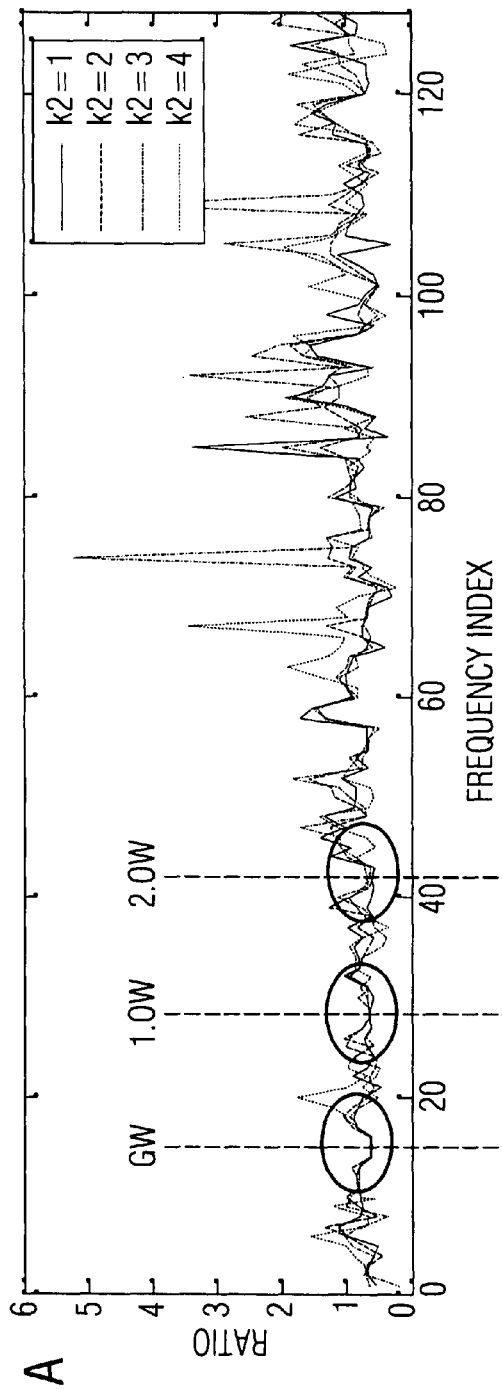
FIG. 21a) depicts an exemplary curve of the quotient between the red transmit channel and the infrared transmit channel at four different points in time k2.
Figure 21B:
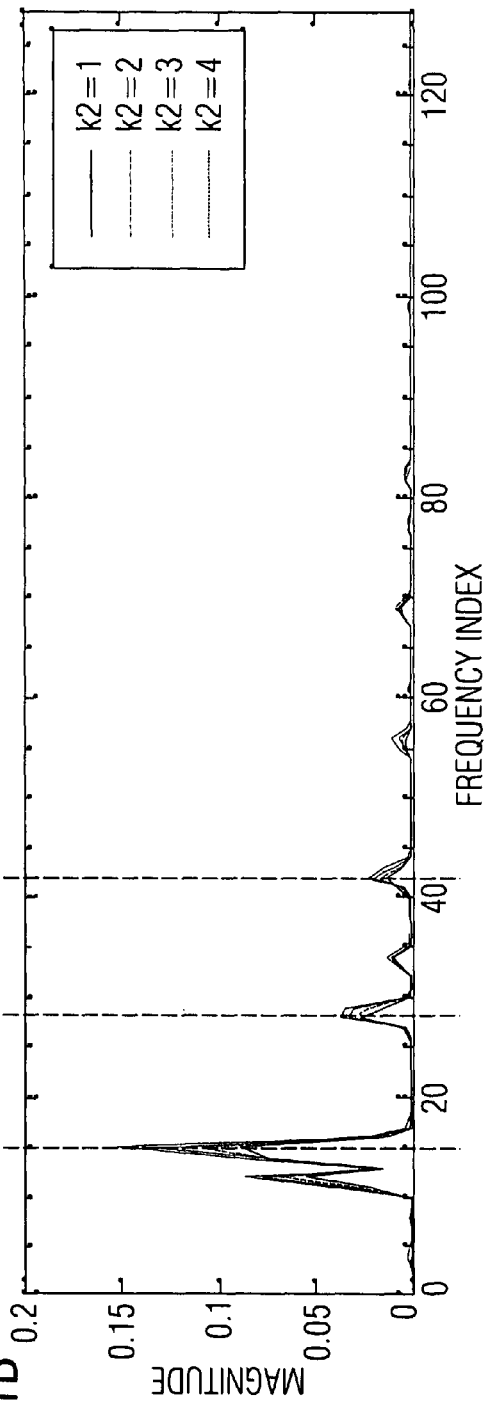
FIG. 21b) shows an exemplary curve of a reference spectrum determined using the method of the complex total least squares fit method.

The function of the spectral mask 340 is to search for the Fourier coefficients of the pulse signal within the spectrum and to set all other coefficients to zero and thus to exclude any frequency portions which do not belong to the pulse signal from further analysis. All other coefficients contribute to an incorrect determination of the linear coefficient $\rho$. To illustrate this, the linear coefficient of the two disturbed spectra (red and infrared) is initially formed on a point-by-point basis, so that a linear coefficient $\rho$ is formed for each individual spectral line, as is depicted in FIGS. 21a) and 21b). FIG. 21a) illustrates the exemplary curve of linear coefficient $\rho$ (referred to as ratio in the figure) from two disturbed spectra of the waveforms of the bright transmit channels, FIG. 21b shows, in this context, the curve of a reference spectrum which has been corrected with regard to the interference. Both spectral curves are plotted at four different points in time, respectively, k2=1.4. If the linear coefficient of the two spectra of FIG. 21a is compared to the reference spectrum across several time windows, it becomes clear that the linear coefficient is correct only above the frequency components of the pulse signal, and is the same for all of these frequencies. Initially, this leads to no appreciable error in computing the linear coefficient with the singular-value decomposition, since using a total least squares fit method, the linear coefficient is more highly weighted at higher amplitudes than at lower amplitudes.

Figure 22:
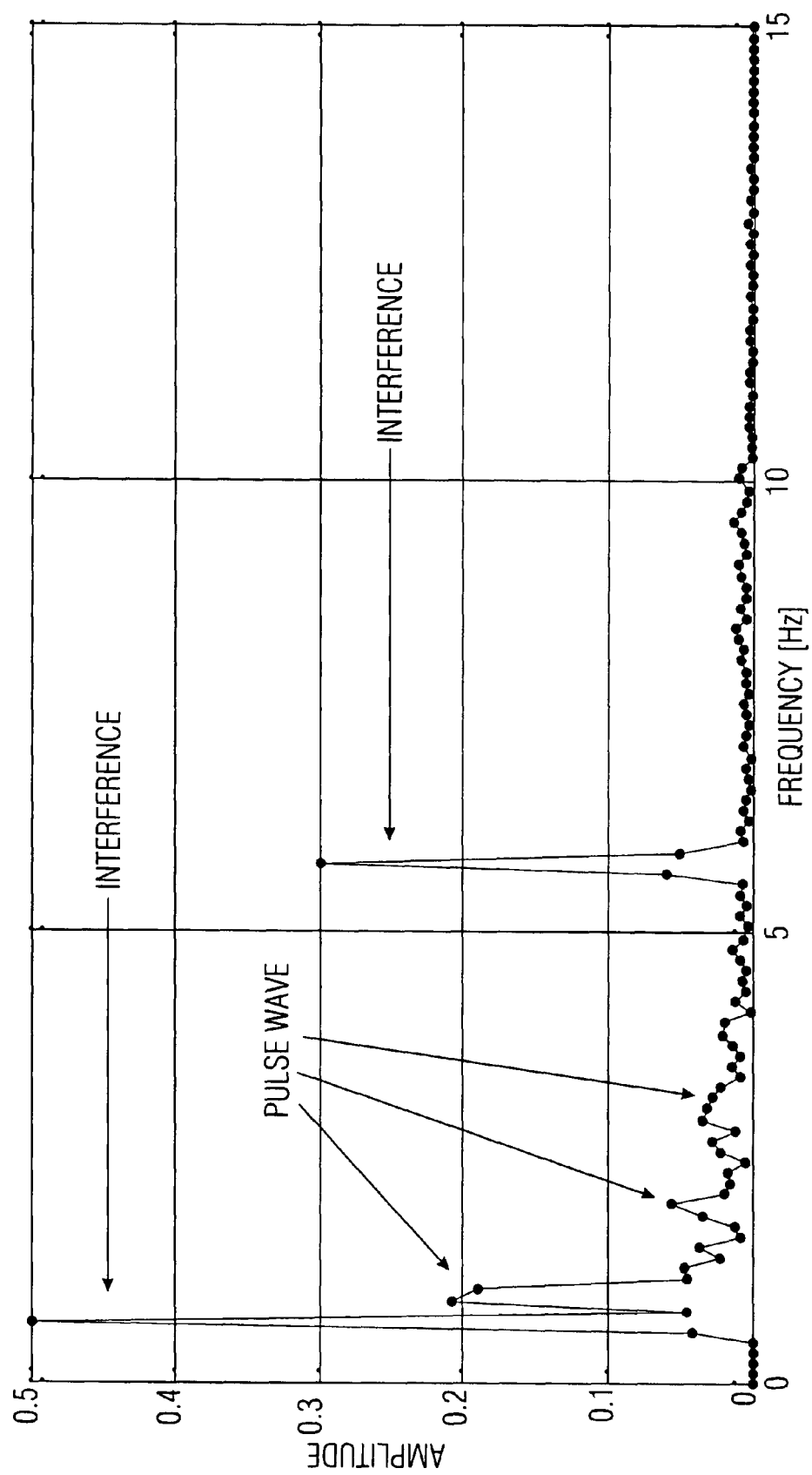
FIG. 22 depicts an exemplary spectrum of a waveform, wherein the amplitudes of the interference are larger than the amplitudes of the pulse wave.

Problem arise when the amplitudes of the interferences become larger than the pulse wave, as is schematically shown in FIG. 22. By way of example, FIG. 22a shows a spectrum of a signals disturbed by interfering signals, the amplitudes of which are larger than the amplitudes of the actual pulse wave. The quotient of two spectra is undefined at the frequencies of an interferer, and it bears no relation to the blood oxygen saturation of a test person. Without the spectral mask 340, dominant features would lead to an incorrect blood oxygen saturation value, as is shown in FIG. 22. Experience has shown that the linear coefficient with such dominant interferers in the spectrum amounts to the value of 1, as the interference is mostly due to light sources which may be found in both spectra with the same amplitude. A linear coefficient equaling 1 signifies a blood oxygen saturation of about 80%, depending on the calibration curve. Without the inventive spectral mask introduced here, interferences which occur in the spectrum in a dominant manner would lead to an unreliable or incorrect $SpO_2$ of about 80% without taking into account the actual saturation in a relevant manner.

The algorithm of the spectral mask is able to differentiate frequency components of the pulse wave from those of the interferers. The algorithm provides a binary mask with elements {0,1}, by which the spectrum may be multiplied on a point-by-point basis so as to suppress those Fourier coefficients which do not belong to the pulse signal.

The spectral mask exhibits an algorithm of the harmonic relation. The method of the harmonic relation is based on findings of examining numerous pulse signals for their spectral properties. The fundamental finding is the harmonic relation of the three relevant frequencies $f_g$ of the fundamental wave, $f_{o1}$ and $f_{o2}$ of the second harmonic. In this context, it is also known that the second harmonic is at double the frequency of the fundamental wave, and that the third harmonic is at three times the frequency of the fundamental wave. On the basis of this relation, a mask may now be created which masks in, in the frequency range, those frequency portions of double and three times the frequency of a fundamental wave, i.e. exhibits a 1 at these locations, and masks out all other frequencies, i.e. has a zero at these locations. A sum may then be formed from the remaining coefficients, the sum being associated with the fundamental frequency. This process may then be repeated for any potential heart frequencies feasible, for example within a range from 30-300 Hz, and subsequently, that frequency at which the sum is maximized may be selected.

A further property which may be taken into account in this context is that the amplitudes of the respective harmonics exhibit a decaying characteristic. This means that at the first harmonic or at double the frequency of the fundamental wave, the amplitude has a smaller amplitude than the fundamental wave itself. At the second harmonic, which has three times the frequency of the fundamental wave, the amplitude is smaller, in turn, than at the first harmonic. Values for which the appropriate condition of the decaying spectrum is not met will not be considered in the search for the maximum.

Figure 23:
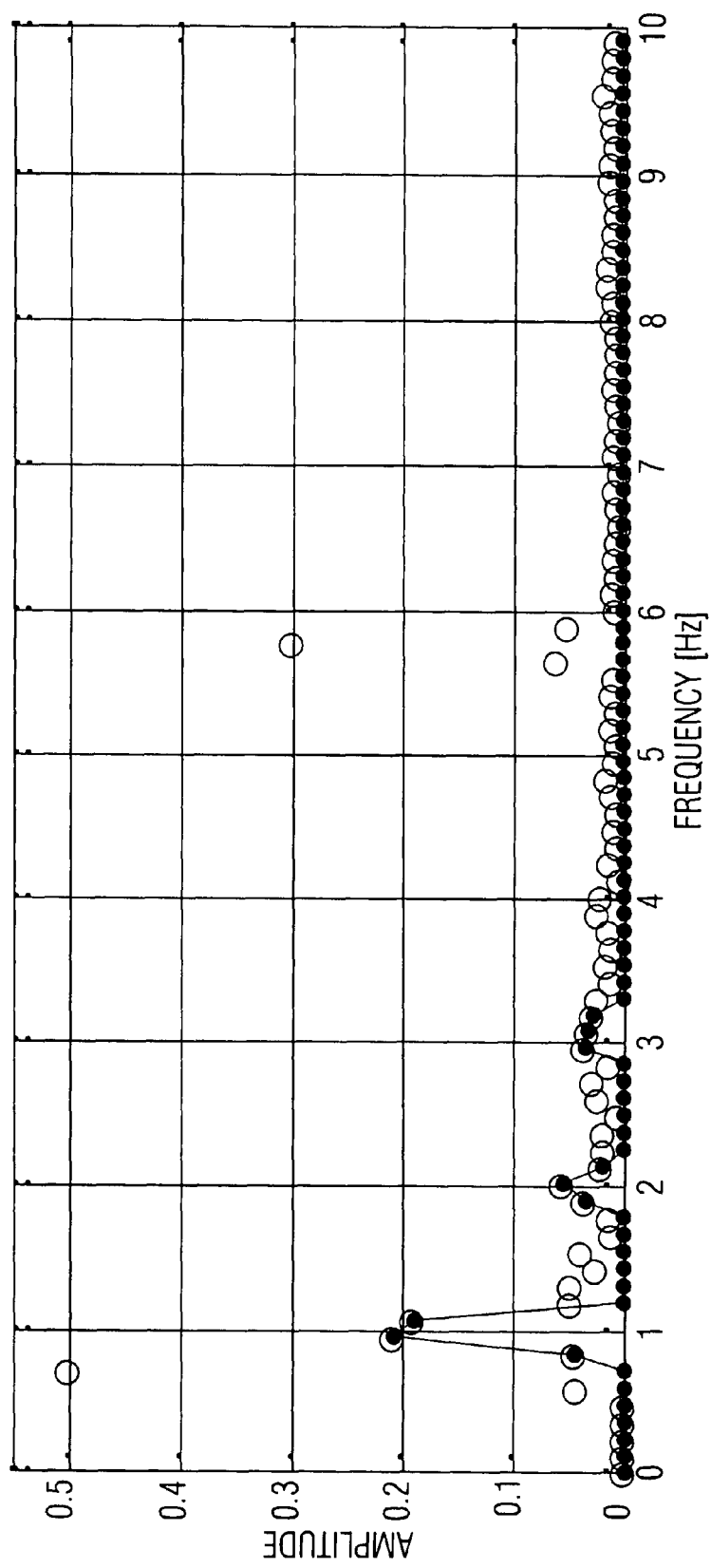
FIG. 23 depicts a reference spectrum (empty circles) and the coefficients selected after applying the spectral mask (full dots)

FIG. 23 shows a reference spectrum (empty dots), and the coefficients selected after applying the spectral mask (full dots). It may be seen that the two interferers at about 0.75 Hertz and 5.75 Hertz can no longer be found in the new spectrum after applying the spectral mask.

Now, the heart frequency may be determined via the position of the spectral mask in the spectrum. In the embodiment of FIG. 3 of the present invention, the heart frequency will then be output at output 345.

As has already been mentioned above, one could compute the linear coefficient ρ already from the first application of the total least squares fit method, however, interferences of high amplitudes here lead to an error in the measured quantity. After multiplication by the spectral mask, only the relevant frequency components are selected. In accordance with the invention, the total least squares fit method with the singular-value decomposition is again applied to the frequency components selected.

Figure 24:
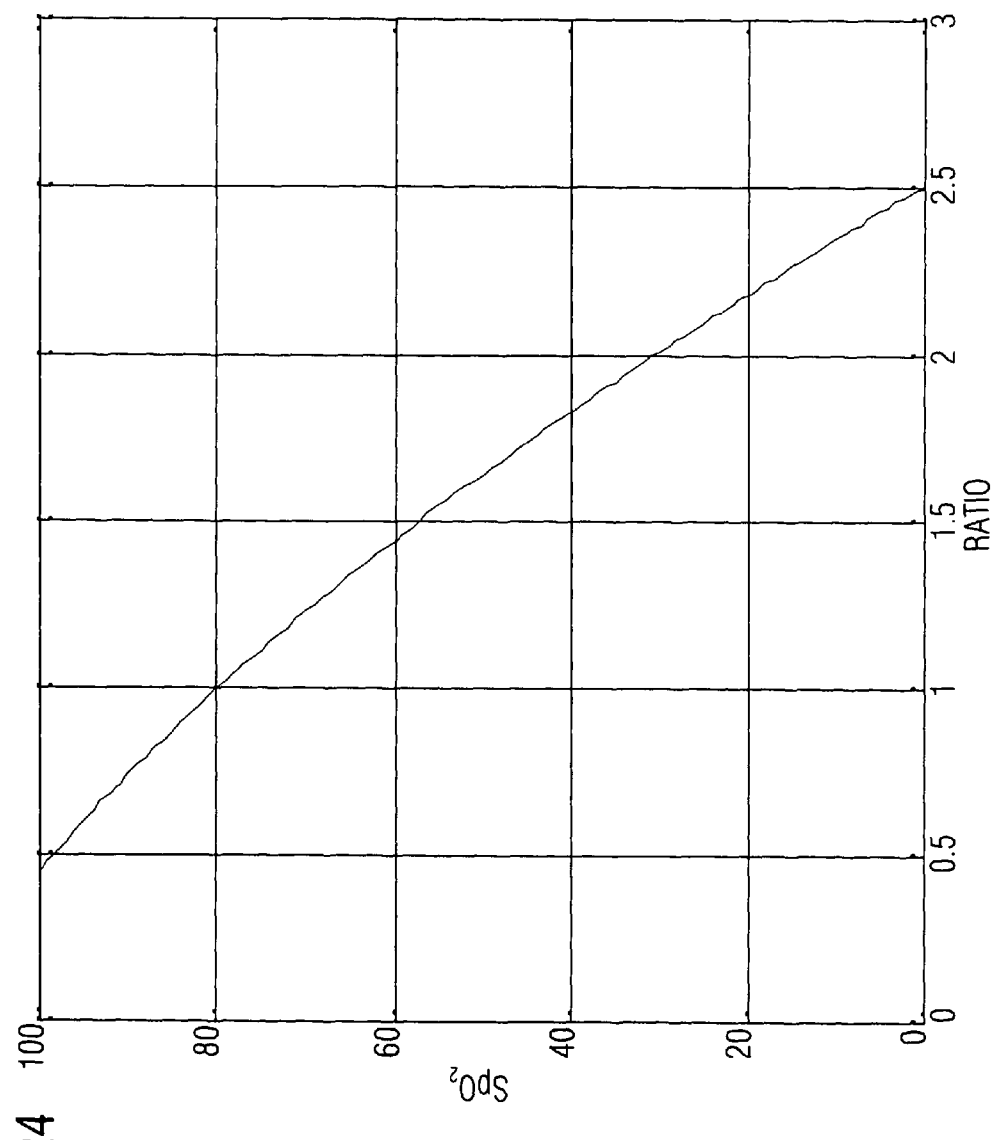
FIG. 24 depicts an exemplary characteristic curve of a calibration function.
Figure 25:
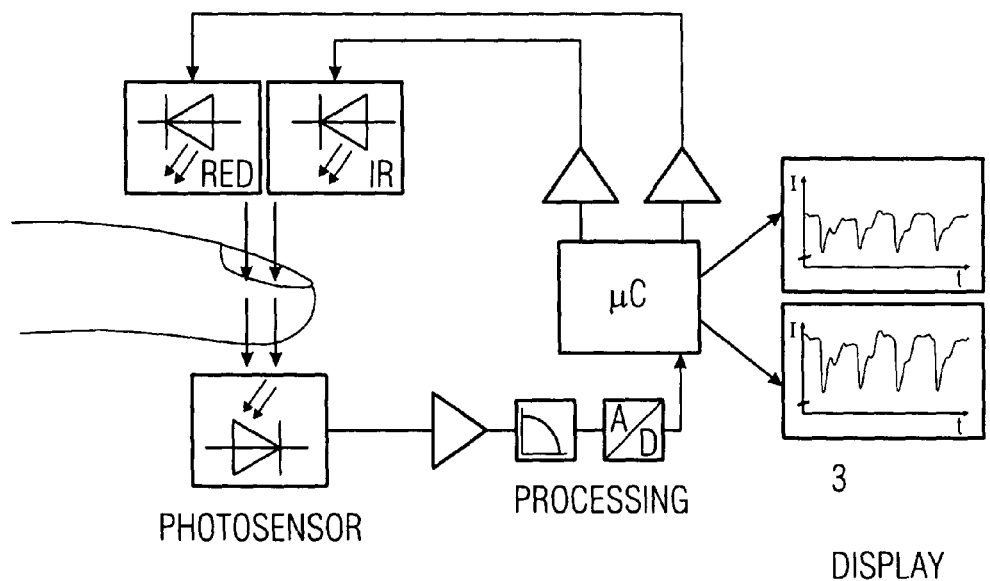
FIG. 25 shows a basic block diagram of the hardware of a pulse oximeter.
Figure 26:
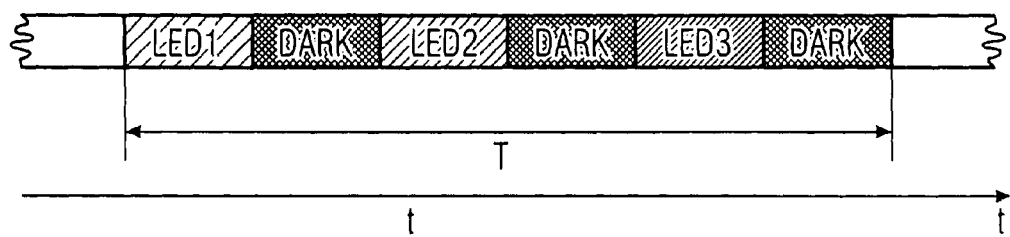
FIG. 26 is a schematized representation of a time division multiple access method (TDMA).

In this context, only those frequency components are used which have been determined by means of the spectral mask. Via these interference-corrected spectra, the original straight line and its slope may now be determined. In addition to the slope of the original straight line, it is also possible to extract, a measure of the reliability of the slope determined, from the matrix decomposition of the over-determined linear equation system. The variance in accordance with the Frobenius norm, which may be directly obtained from the matrix decomposition, indicates the similarity of the two signals. The variance is used as an indictor of excessive interference effects which prevents the computation of the physiological parameters within the specified tolerance range. Then this variance can be output at output 355 in accordance with FIG. 3. The complex total least squares fit method has a calibration function 360 connected downstream from it. The slope of the original straight line which has been determined using the complex total least squares fit method and which is representative of the blood saturation value of the test person is passed on to a calibration function 360. The calibration function directly associates $SpO_2$ values (blood saturations values) with the slope values obtained. The respective $SpO_2$ values are then output, in accordance with FIG. 3, at output 365. FIG. 24 shows an exemplary characteristic curve of a calibration function. It can be seen how blood saturation values ($SpO_2$ values) are associated with quotients (ratio). The characteristic curves of the calibration function are empirically determined using reference measurements.

One advantage of the present invention is that it enables a spectral analysis which is specifically tailored to the field of application of plethysmography and pulse oximetry and which significantly improves the reliability of the plethysmograms, and enables an effective measure of suppressing interferences by, for example, electromagnetic fields (e.g. high-frequency surgery).

Another advantage is that using singular value decomposition for calculating $SpO_2$ values from the complex spectra, a measure of reliability in the form of a variance may be extracted and used for assessing the quality of the result, or that a malfunction may be reliably detected in this manner.

An additional advantage is that using the inventive apparatus for measuring the blood oxygen saturation and heart frequency, reliable measurements may be made even at a low arterial blood volume pulsation while the patient is moving, which is due to the reliability obtained by the inventive method.

In general terms, one may state that the quality of treatment for a patient, in particular in intensive care and in operating rooms, may be considerably improved by the present invention. Due to the increased reliability and robustness of the method, diagnostic errors due to distorted measurements and/or due to unreliable measurement values can be considerably reduced.

Thus, the increased reliability of the measurement directly causes an increase in the quality of treatment for a patient. Thus, one advantage of the present invention is the fact that due to the increased reliability of the measurement values of a pulse oximeter, in particular in critical environments such as operating rooms or intensive-care units, increased chances of recovery and more efficient methods of treatment are enabled.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for determining a spectral ratio between a first signal comprising a first spectrum which depends on a biological quantity, and a second signal comprising a second spectrum which depends on a biological quantity, the first signal and the second signal comprising a plurality of harmonics of a periodic signal, the apparatus comprising:

a computer for computing a first wave ratio between a spectral value of the first spectrum at a first frequency which comprises a harmonic of the plurality of harmonics, and a spectral value of the second spectrum at the first frequency;

and for computing a second wave ratio between a spectral value of the first spectrum at a second frequency which comprises another harmonic of the plurality of harmonics, and a spectral value of the second spectrum at the second frequency;

an optimizer for determining the spectral ratio while using the first and second wave ratios, the optimizer being adapted to determine the spectral ratio such that it differs from the first wave ratio and the second wave ratio, and meets an optimization criterion, wherein the computer is adapted to pass on a plurality of the spectral values of the two spectra to the optimizer as tuples of a frequency, wherein the spectral values are complex spectral values, wherein the optimizer is adapted to determine a regression line from the plurality of tuples of the complex spectral values, the actual or perpendicular square distance from the tuples to the regression line being minimized as the optimization criterion, and wherein the optimizer is adapted to determine the regression line by applying the total least squares fit method, and the spectral ratio depends on the regression line.

2. The apparatus as claimed in claim 1, wherein the period of the periodic signal is independent of the biological quantity.

3. The apparatus as claimed in claim 1, wherein the first signal and the second signal depend on the biological quantity in different ways.

4. The apparatus as claimed in claim 1, wherein the first and second signals exhibit dependencies on the biological quantity in the plurality of harmonics.

5. The apparatus as claimed in claim 1, wherein the biological quantity is a blood oxygen saturation or a heart frequency.

6. The apparatus as claimed in claim 1, wherein the computer is adapted to compute the first wave ratio at a fundamental wave frequency of the periodic signal, and the second wave ratio at a harmonic frequency of the periodic signal.

7. The apparatus as claimed in claim 1, wherein the computer is adapted to form wave ratios between a plurality of spectral values of the first and second signals, and wherein, in addition, the optimizer is adapted to form the spectral ratio from the plurality of wave ratios.

8. The apparatus as claimed in claim 1, wherein the signals originate from a transillumination of a tissue of a test person.

9. The apparatus as claimed in claim 1, wherein one signal is based on an infrared light receive signal, and one signal is based on a red light receive signal.

10. The apparatus as claimed in claim 1, wherein the optimizer is adapted to optimize a cumulated distance measure between the spectral ratio and the wave ratios.

11. The apparatus as claimed in claim 1, wherein the optimizer is adapted to determine the regression line using a singular-value decomposition of a matrix, the two signals forming the columns of the matrix, and that singular value which is smaller, in magnitude, of the singular-value decomposition being set to zero for linearizing the equation system.

12. The apparatus as claimed in claim 1, further comprising a provider for providing the first and second signals, and further being adapted to reduce frequency portions on the basis of previous knowledge of the spectral curve of a signal portion.

13. The apparatus as claimed in claim 12, wherein the provider for providing the first and second signals is adapted to reduce other spectral portions on the basis of known intensity ratios between the harmonics.

14. The apparatus as claimed in claim 12, wherein the provider for providing the first and second signals is adapted to provide only spectral portions of the fundamental wave, of the first harmonic, and of the second harmonic of the periodic signal.

15. The apparatus as claimed in claim 12, wherein the provider for providing the first and second signals is adapted to provide only those signal portions of signals which correspond to a pulse signal of a living being in terms of their frequency and amplitude ratios.

16. The apparatus as claimed in claim 12, wherein the provider for providing the first and second signals is adapted to determine, on the basis of a reference spectrum, pulse signal portions of a living being, and to mask out other frequencies from the signals.

17. The apparatus as claimed in claim 1, wherein the computer is adapted to pass the signals on to the optimizer, and wherein the optimizer is adapted to determine, on the basis of the spectra of the signals, a reference spectrum for which a distance measure in relation to the spectra of the signals is optimized.

18. The apparatus as claimed in claim 1, wherein the two signals originate from a plethysmogram.

19. The apparatus as claimed in claim 1, comprising a second provider for providing a first time-discrete reference signal which exhibits a first interference portion, and a second time-discrete reference signal which exhibits a second interference portion, the second interference portion being shifted in phase relative to the first interference portion;
and a subtractor for generating a differential signal from the two reference signals, the differential signal comprising a frequency component being caused by the first and second interference portions, and a manipulator for manipulating the two signals, on the basis of the differential signal, such that the frequency component is reduced in a manipulated signal; and
the manipulated time-discrete signal is made available to the computer.

20. The apparatus as claimed in claim 1, comprising a first provider for providing the time-discrete signal, the provider being adapted to sample an iterating optical signal which corresponds to a bright period during which a transmit light source adopts an on state, and comprising a second provider for providing a time-discrete reference signal adapted to sample two optical signals which correspond to dark periods during which no transmit light source adopts an on state.

21. The apparatus as claimed in claim 1, comprising a first provider for providing a time-discrete signal, the provider being adapted to process an iterating optical signal, the optical signal comprising sequences and comprising a sequence of at least two bright periods during which a transmit light source adopts an on state, and comprising at least one dark period during which no transmit light source adopts the on state, and wherein the at least two bright periods are irregularly arranged within a sequence, and the provider for providing the time-discrete signal further being adapted to make available the time-discrete signal in accordance with a bright transmit signal on the basis of the information about the arrangement of the bright periods in the sequence.

22. The apparatus as claimed in claim 21, wherein the sequence of an optical signal is based on a clock, in accordance with which the bright and dark periods occur.

23. The apparatus as claimed in claim 22, wherein the provider for providing the time-discrete signals are adapted to operate at a clock higher than 800 Hz.

24. The apparatus as claimed in claim 1, wherein the signals originate from a spread spectrum modulation.

25. A method for determining a spectral ratio between a first signal comprising a first spectrum which depends on a biological quantity, and a second signal comprising a second spectrum which depends on a biological quantity, the first signal and the second signal comprising a plurality of harmonics of a periodic signal, the method comprising:
computing a first wave ratio between a spectral value of the first spectrum at a first frequency which comprises a harmonic of the plurality of harmonics, and a spectral value of the second spectrum at the first frequency;
computing a second wave ratio between a spectral value of the first spectrum at a second frequency which comprises another harmonic of the plurality of harmonics, and a spectral value of the second spectrum at the second frequency;
determining the spectral ratio while using the first and second wave ratios, the spectral ratio being determined such that it differs from the first and second wave ratios and meets an optimization criterion,
wherein the step of determining comprises:
passing on a plurality of the spectral values of the two spectra as tuples of a frequency, and
wherein the spectral values are complex spectral values,
computing a regression line from the plurality of tuples of the complex spectral values, the actual or perpendicular square distance from the tuples to the regression line being minimized as the optimization criterion, wherein the regression line is determined in accordance with the total least squares fit method, and the spectral ratio depends on the regression line.

* * * * *